(12) United States Patent
Garner-Richards et al.

(10) Patent No.: US 9,089,366 B2
(45) Date of Patent: Jul. 28, 2015

(54) SYSTEM FOR TRACKING SURGICAL OBJECTS

(71) Applicant: Steven Garner-Richards, Endicott, NY (US)

(72) Inventors: Steven Garner-Richards, Endicott, NY (US); Thomas Rispoli, Endicott, NY (US)

(73) Assignee: Steven Garner-Richards, Homosassa, FL (US)

( * ) Notice: Subject to any disclaimer, the term of this patent is extended or adjusted under 35 U.S.C. 154(b) by 43 days.

(21) Appl. No.: 14/132,733

(22) Filed: Dec. 18, 2013

(65) Prior Publication Data

US 2014/0303606 A1    Oct. 9, 2014

Related U.S. Application Data

(60) Provisional application No. 61/808,338, filed on Apr. 4, 2013.

(51) Int. Cl.
*G06F 17/00* (2006.01)
*A61B 19/00* (2006.01)
(Continued)

(52) U.S. Cl.
CPC ........... *A61B 19/44* (2013.01); *A61B 17/06066* (2013.01); *A61B 17/06114* (2013.01); *A61B 19/026* (2013.01); *A61F 13/44* (2013.01); *A61B 2019/0267* (2013.01); *A61B 2019/442* (2013.01);
(Continued)

(58) Field of Classification Search
USPC ......... 235/375, 385; 604/362, 286; 340/572.1
See application file for complete search history.

(56) References Cited

U.S. PATENT DOCUMENTS 3,630,202 A    12/1971  Small
3,800,792 A     4/1974  McKnight et al.
(Continued)

FOREIGN PATENT DOCUMENTS

EP    1032911 B1    6/2004
EP    2399559 A1   12/2011
(Continued)

OTHER PUBLICATIONS

Partial International Search dated Jul. 28, 2014 for PCT/US204/031541.
(Continued)

*Primary Examiner* — Ahshik Kim
(74) *Attorney, Agent, or Firm* — Brown & Michaels, PC

(57) ABSTRACT

Methods and apparatus track surgical objects placed in a body cavity so that they may be reliably located and recovered from the body cavity at a later time. In one preferred embodiment, an apparatus comprises a vibrantly colored stringer threaded through apertures in a plurality of surgical objects and vibrantly colored tracking tags affixed to each end of the vibrantly colored stringer to maintain the surgical objects on the vibrantly colored stringer. In alternate embodiments, photo-reactive pigments in the range of 345-375 nm are also added to the vibrantly colored stringer and vibrantly colored tracking tags to enhance their visual detection under ambient lighting, when illuminated with a spectrum specific light source, and/or viewed through a spectrum-specific transmission filter in the same range of wavelengths. In another embodiment, retainers having apertures through which the vibrantly colored stringer may be threaded and bodies formed to be replacably affixed to a variety surgical objects are also employed.

44 Claims, 23 Drawing Sheets

(51) Int. Cl.
*A61B 17/06* (2006.01)
*A61F 13/44* (2006.01)
*A61B 19/02* (2006.01)

(52) U.S. Cl.
CPC ..... *A61B 2019/444* (2013.01); *A61B 2019/446* (2013.01); *A61B 2019/4821* (2013.01)

(56) References Cited

U.S. PATENT DOCUMENTS

| | | | |
|---|---|---|---|
| 3,840,015 | A | 10/1974 | Gain |
| 3,941,132 | A | 3/1976 | Lenaghan |
| 4,244,369 | A | 1/1981 | McAvinn et al. |
| 4,671,916 | A | 6/1987 | Hamas |
| 4,917,694 | A | 4/1990 | Jessup |
| 4,966,595 | A | 10/1990 | Meringola |
| 4,983,173 | A | 1/1991 | Patience et al. |
| 5,009,652 | A | 4/1991 | Morgan et al. |
| 5,041,103 | A | 8/1991 | Vytautas |
| 5,045,080 | A | 9/1991 | Dyer et al. |
| 5,049,219 | A | 9/1991 | Johns et al. |
| 5,074,840 | A | 12/1991 | Yoon |
| 5,112,325 | A | 5/1992 | Zachry |
| 5,203,767 | A | 4/1993 | Cloyd |
| 5,456,718 | A | 10/1995 | Szymaitis |
| 5,573,529 | A | 11/1996 | Hank et al. |
| 5,610,811 | A | 3/1997 | Honda |
| 5,664,582 | A | 9/1997 | Szymaitis |
| 5,923,001 | A | 7/1999 | Morris et al. |
| 6,026,818 | A * | 2/2000 | Blair et al. .................... 128/899 |
| 6,223,137 | B1 | 4/2001 | McCay et al. |
| 6,366,206 | B1 | 4/2002 | Ishikawa et al. |
| 6,777,623 | B2 | 8/2004 | Ballard |
| 6,998,541 | B2 | 2/2006 | Morris et al. |
| 7,005,556 | B1 | 2/2006 | Becker et al. |
| 7,297,834 | B1 | 11/2007 | Shapiro |
| 7,399,899 | B2 | 7/2008 | Fabian |
| 7,465,847 | B2 | 12/2008 | Fabian |
| 8,726,911 | B2 * | 5/2014 | Blair ............................. 128/899 |
| 2001/0025155 | A1 | 9/2001 | Yoon |
| 2002/0029032 | A1 | 3/2002 | Arkin |
| 2003/0006762 | A1 * | 1/2003 | Clements ...................... 324/239 |
| 2003/0066537 | A1 | 4/2003 | Fabian et al. |
| 2004/0129279 | A1 * | 7/2004 | Fabian et al. ................. 128/899 |
| 2005/0049564 | A1 * | 3/2005 | Fabian .......................... 604/362 |
| 2005/0222617 | A1 | 10/2005 | Ororz, Jr. |
| 2007/0083170 | A1 | 4/2007 | Stewart et al. |
| 2007/0160494 | A1 * | 7/2007 | Sands ............................ 422/26 |
| 2008/0238631 | A1 | 10/2008 | Blake et al. |
| 2009/0114701 | A1 | 5/2009 | Zemlok et al. |
| 2010/0179822 | A1 | 7/2010 | Reppas |
| 2011/0264138 | A1 | 10/2011 | Avelar et al. |
| 2012/0238906 | A1 | 9/2012 | Gilchrest et al. |
| 2013/0079590 | A1 | 3/2013 | Bengtson |
| 2013/0088354 | A1 | 4/2013 | Thomas |

FOREIGN PATENT DOCUMENTS

| | | |
|---|---|---|
| EP | 2476379 A1 | 7/2012 |
| GB | 1422414 A | 1/1976 |
| JP | 2010282250 A | 12/2010 |
| WO | 93/24086 | 12/1993 |
| WO | 9324086 | 12/1993 |
| WO | 95/27252 | 10/1995 |
| WO | 9527252 | 10/1995 |
| WO | 02/19918 A2 | 3/2002 |
| WO | 0219918 A2 | 3/2002 |
| WO | 2010/028085 A2 | 3/2010 |
| WO | 2010028085 A2 | 3/2010 |

OTHER PUBLICATIONS

International PCT Search Report for PCT/US2014/031541; Sep. 24, 2014; 16 pages.
Opthamology Innovation Network, "Anodized Instruments . . . The new Look for Opthalmic Instruments" Jan. 14, 2013, 4 pages. http://www.katalystsurgical.com/oin/articles/anodized-instruments-the-new-look-for-ophthalmic-instruments/.
Spectrum, "Color Coded Instruments", website catalog, May 8, 2013, http://www.spectrumsurgical.com/color-coding.php.
Vibracoat America Inc. "Powder Coating Chart" 7 pages, May 9, 2013, http://www.vitracoat.com/COLOR_MATCH2/PanelMuestreo.asp.

* cited by examiner

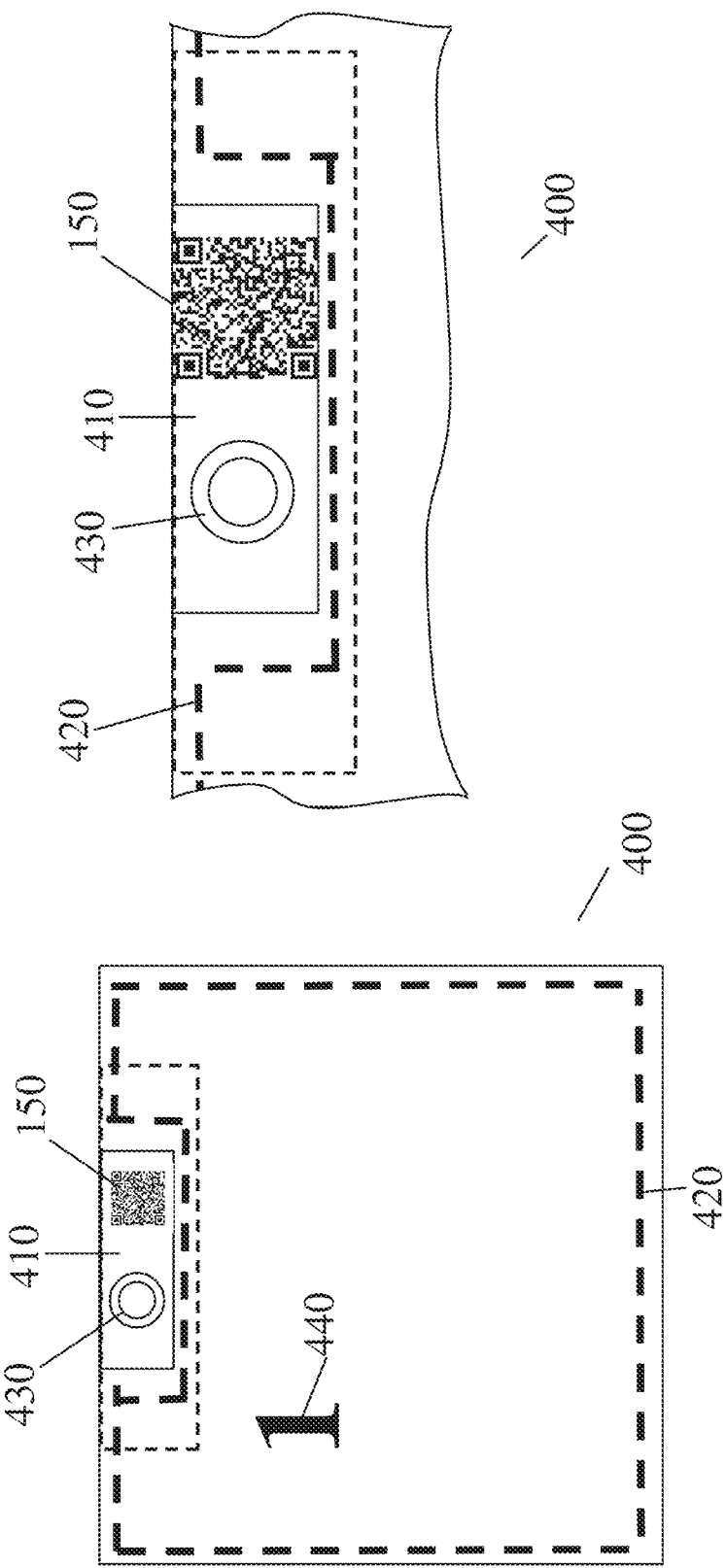

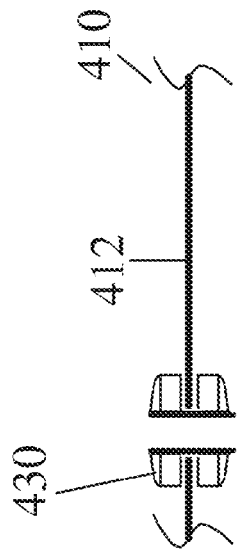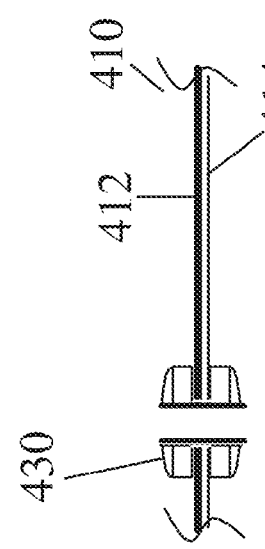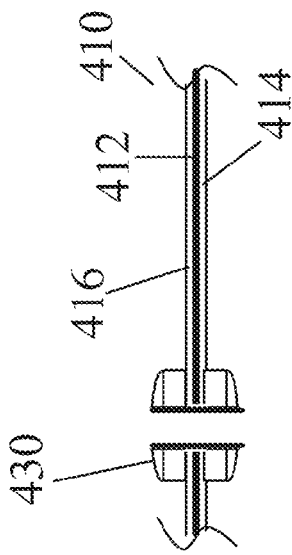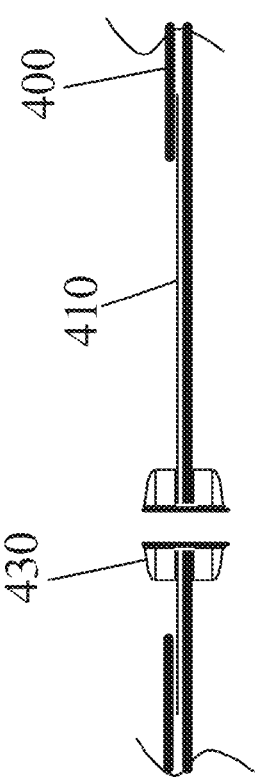

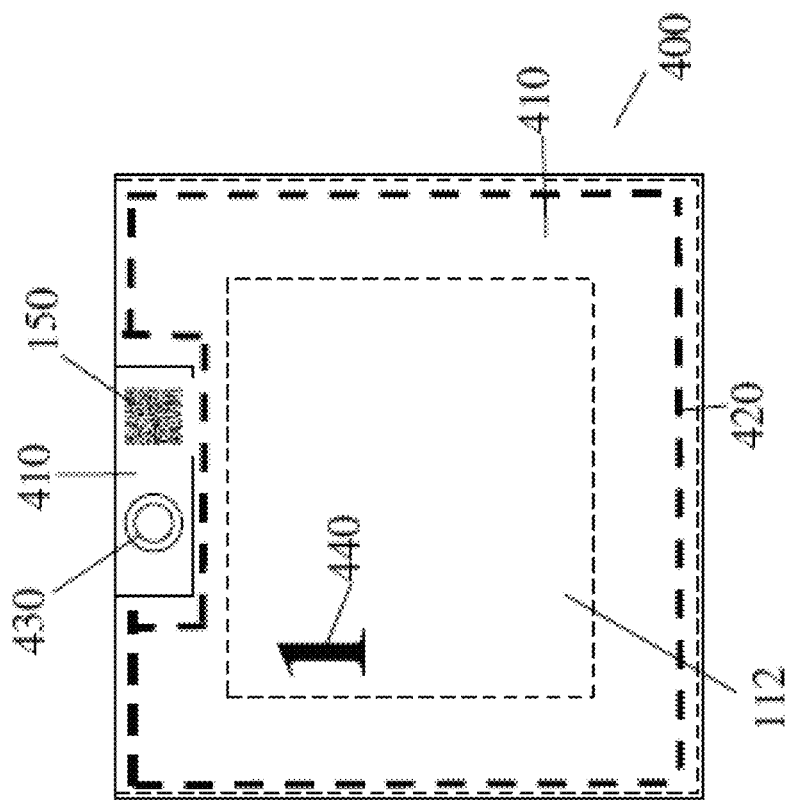
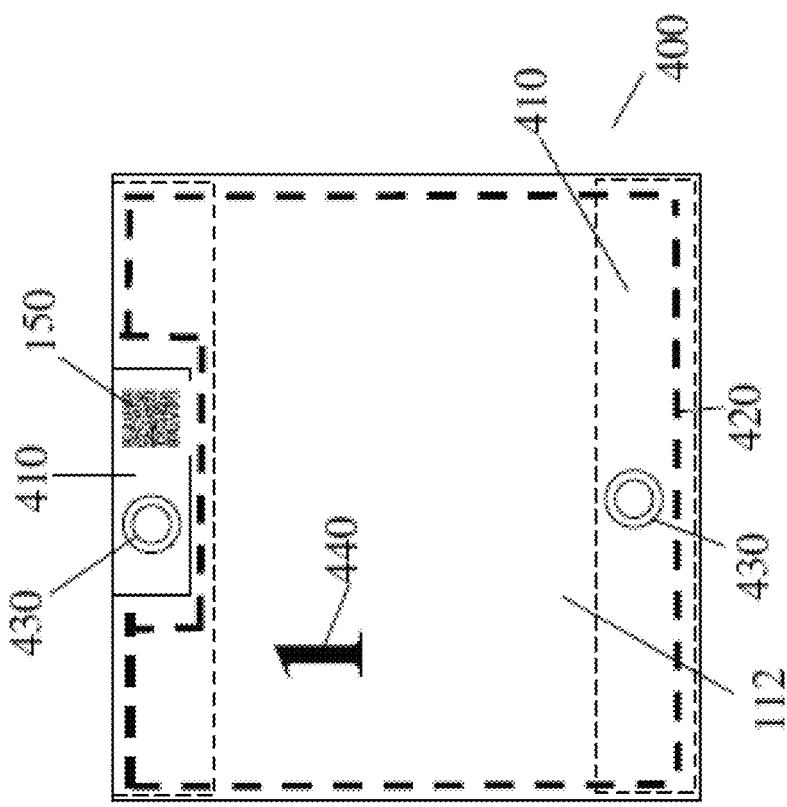

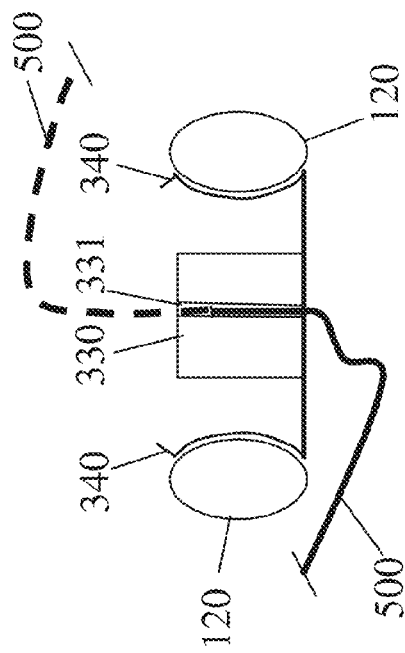
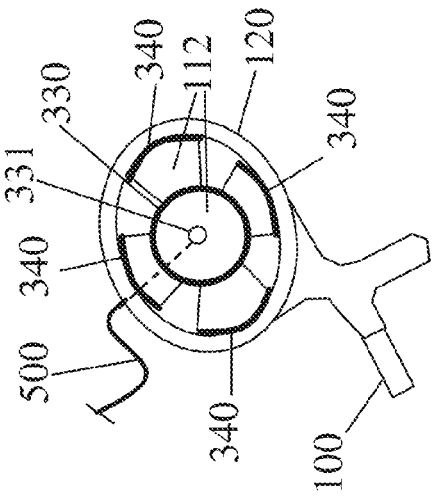
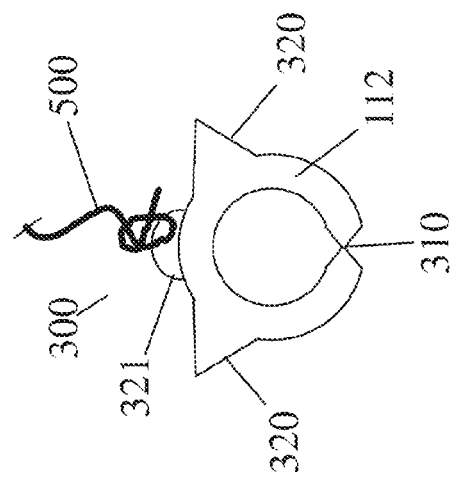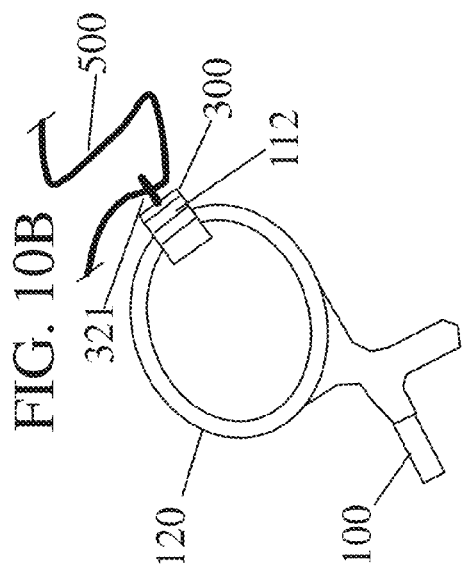

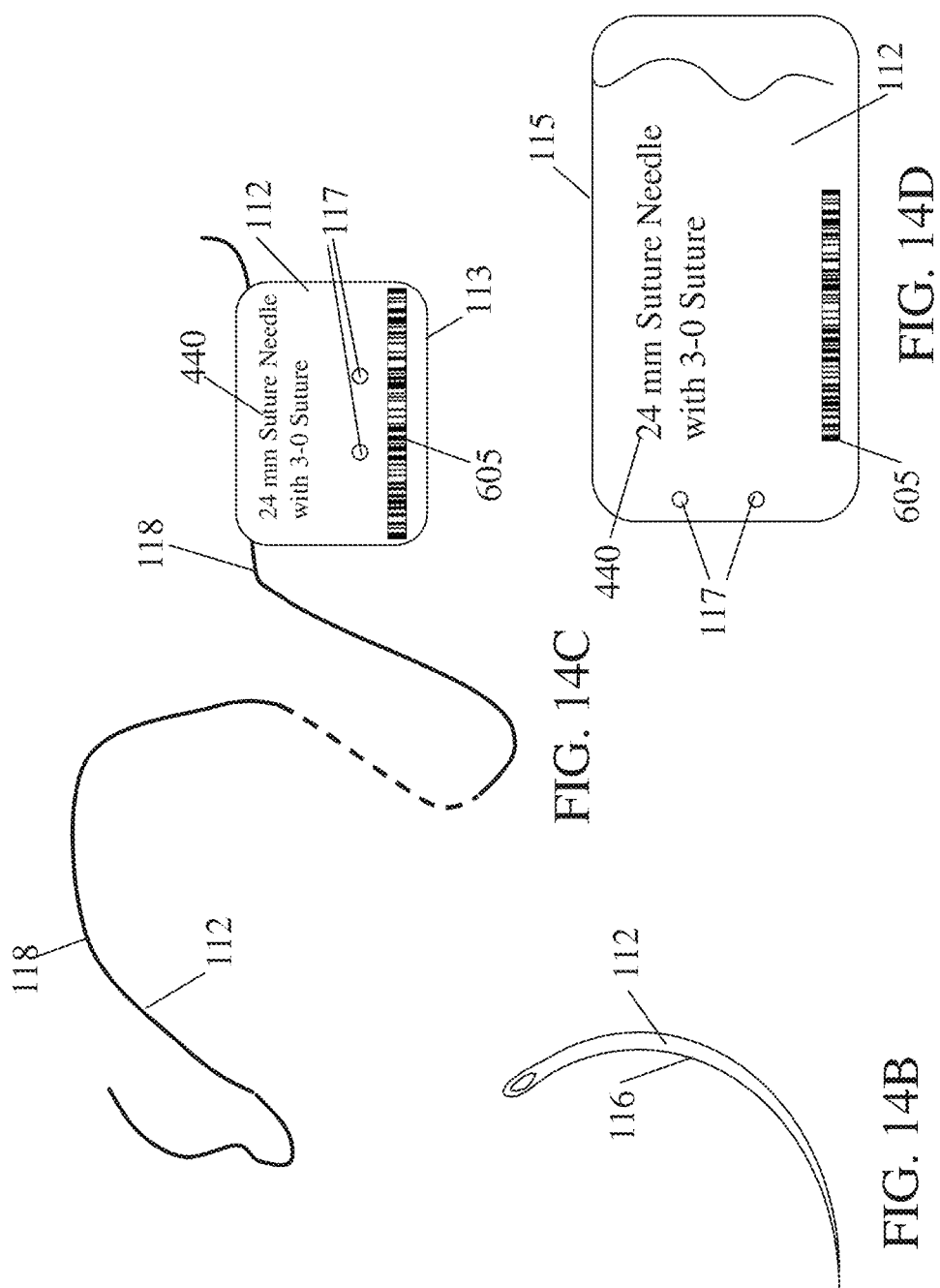

SYSTEM FOR TRACKING SURGICAL OBJECTS

REFERENCE TO RELATED APPLICATIONS

This application claims one or more inventions which were disclosed in Provisional Application No. 61/808,338, filed Apr. 4, 2013, entitled "System for Tracking Surgical Objects". The benefit under 35 USC §119(e) of the United States provisional application is hereby claimed, and the aforementioned application is hereby incorporated herein by reference.

BACKGROUND OF THE INVENTION

1. Field of the Invention

The invention pertains to the field of surgical devices. More particularly, the invention pertains to tracking of surgical objects placed in a human or animal body.

2. Description of Related Art

Surgical practice often requires placing surgical objects in the human body that may remain in place for at least a portion of the duration of a surgical procedure. These objects include, but are not limited to, surgical instruments such as forceps, scalpels, surgical needles, sutures, and clamps of various designs, gauze pads of various construction, and surgical sponges of various materials, design, and construction. Surgical teams have implemented procedures to try to ensure that all objects are removed from the human body prior to closing the surgical field and sending the patient to recovery.

The primary method of tracking surgical objects involves manual counting of objects prior to and during surgery, and recounting them as they are recovered from the surgical field. A third count is also preferably taken to recheck the results. The count of objects introduced into the surgical field must obviously equal the count of objects recovered from the surgical field at the end of the surgical procedure.

This practice is, however, prone to human error as miscounts can occur. In such cases, surgical instruments, gauze pads, sponges, or other surgical objects may be left in the body. Alternatively, used gauze pads, sponges, or other similar objects may stick together, and result in a miscount such that the surgeon believes an object has been left in the body, when in fact none has been.

In the event an object is left in the body, physiological foreign body responses can lead to infection and death, and movement of objects such as clamps can lead to physical damage in surrounding organs, also leading to sepsis and death. Hence, accurate accounting of surgical objects is critical; not only from a patient safety standpoint, but also from a liability standpoint as such instances often result in malpractice law suits regardless of patient outcome.

To further complicate this situation, first responders must often pack wounds with gauze, sponges, or other objects during stabilization, triage, and transit to an emergency room before handing the patient off to physicians for further treatment. Particularly in cases of multiple traumas, where triage protocol dictates focusing on immediate treatment of one area of the body while simply stabilizing other wounds, confusion can result. Examples of such cases include multiple gun-shot wounds, multiple shrapnel wounds, and others. In this situation, attending physicians may also not receive an accurate accounting of objects placed in the body and overlook items placed by first responders.

Szymaitis (U.S. Pat. No. 5,456,718) describes an apparatus for detecting objects within the human body. A strip, when exposed to an alternating electromagnetic field, causes a detectable change in the applied field. The device includes a tagging strip and a hand-held excitation/detector system.

The device requires the use of non-magnetic surgical tables. In addition, false positives are possible due to stray fields produced by other equipment in the surgical suite, and therefore a pre-scan detection of undesired signals, as well as a method providing for their cancellation, may be required.

The conducting strips embedded in the tags work optimally only under certain geometric conditions. However, multiple folding of such strips may occur when, for example, sponges are packed in the body cavity, altering the optimal geometry for the tagging strips to work effectively. Further, the range of sizes and configurations of surgical devices may provide a further impediment to effective use of the tagging strips as the response the tagging strips create in the applied field is dependent on the length of the strips. This may be an issue particularly in smaller surgical objects that are most prone to being overlooked in the body.

Another method to localize items in the body uses X-rays. However, post-operative x-ray examination is not routine as it generally unnecessarily exposes patients to ionizing radiation, and also increases the cost of procedures.

SUMMARY OF THE INVENTION

The stringer systems and methods described herein significantly reduce the likelihood of inadvertently leaving surgical objects in a patient after surgery. Generally, the stringer system includes a stringer (also referred to as a "lanyard") providing a connection to surgical objects along the length of the stringer, and tracking tags affixed to the ends of the stringer. Following the stringer along its length from a tracking tag on one end, to a tracking tag on the other end, allows surgical personnel to ensure that all surgical objects connected to the stringer can be localized and recovered from the surgical site. In some embodiments, a single surgical object is used in conjunction with the stringer, and a single tracking tag, forming a lanyard.

One preferred embodiment includes a stringer system for connecting gauze pads, sponges, other surgical pads of various constructions, or a variety of surgical instruments. Reinforcement of the pads or sponges (hereafter all generically referred to as "sponges") in some preferred embodiments allows for stringer attachment, and application of computer readable optical codes, human readable codes, and other indicia.

In other embodiments, the stringer system includes various retainers that provide for attachment of the stringer system to structures of surgical instruments, such as finger loops of clamps, which may be used in large numbers in some procedures.

In various embodiments, high visibility vibrant coatings are applied to the external surface of the stringer system elements, or appropriate colorants are integrated into their manufacturing materials to achieve the same effect. In other preferred embodiments, spectrum-specific fluorescent, UV-A reactive or luminous pigments are also, or alternatively, added to the coatings or materials of construction to enhance detection.

Further, in some preferred embodiments, tracking tags, similarly prepared for visual detection with vibrant, and in some embodiments fluorescent, UV-A reactive, or luminous, pigments not naturally found in biological structures, are applied to the stringer system to help track the objects attached to the stringer system. Fixation of at least one tracking tag outside the surgical field, and the path of the stringer attached to it through the surgical field, provides an unambiguous indication of the presence and location of surgical objects in the body.

In still other embodiments, computer readable indicia are applied to semi-automate or augment pre-/post-operative surgical object count procedures. Similarly, peel-and-stick labels used in conjunction with a tote board located in the surgical suite are used in some embodiments for further certainty in tracking surgical objects connected by the stringer system.

The elements of the stringer system may also be used as a method of tracking and accounting for surgical objects placed in the surgical field. According to this method, surgical objects connected to the stringer system are placed in the surgical field, and removed from the surgical field when no longer needed by following the stringer along its length from one tracking tag to another. In some embodiments of the method, once removed from the field, surgical objects connected to the stringer system may be accounted for by comparing listings (either manual or computerized) of objects present on the stringer system prior to use to listings after use, to verify all surgical objects introduced into the surgical field have been recovered.

In other embodiments, a method of locating surgical objects in a surgical field uses a tracking tag having a vibrant coating, a lanyard attached to the tracking tag and a surgical object retainer attached to the lanyard. The method attaches the surgical object retainer to a surgical object. When the surgical object is used in surgery in a patient's body, the tracking tag is attached to a position outside the patient's body, such that the tag remains visible even if the surgical object is obscured.

In another embodiment, a method of locating surgical needles in a surgical field uses a tracking tag having a vibrant coating and a surgical needle retainer on the tag. Before surgery, a surgical needle is inserted into the surgical needle retainer. The tracking tag is attached to a position outside a surgical field, such that the tag remains visible. The surgical needle is removed from the surgical needle retainer for use. Before ending surgery, it is confirmed that the surgical needle has been replaced in the surgical needle retainer.

BRIEF DESCRIPTION OF THE DRAWINGS

FIG. 8A shows a surgical sponge having a reinforced layer, with a grommet aperture and indicia applied to the reinforced layer and surgical sponge.

FIG. 8B shows a detail of the reinforced layer of the surgical pad of FIG. 8A.

FIG. 8C shows a detail of a single layer reinforcement, and a grommet aperture.

FIG. 8D shows a detail of a single layer reinforcement, and a grommet aperture.

FIG. 8E shows a detail of a dual layer reinforcement, and a grommet aperture.

FIG. 8F shows a detail of a triple layer reinforcement, and a grommet aperture.

FIG. 8G shows a surgical sponge with two reinforcement layers each having a grommet aperture.

FIG. 8H shows a surgical sponge with a circumferential reinforcement layer having a grommet aperture.

FIG. 10A shows a split-ring retainer attached to a forceps.

FIG. 10B shows a side view of a split-ring retainer.

FIG. 10C shows an orifice retainer attached to a forceps.

FIG. 10D shows a cross-section of an orifice retainer to a forceps.

FIG. 14B shows a surgical needle with a vibrant coating applied.

FIG. 14C shows a surgical suture with a vibrant coating applied and a tracking tag affixed to one end of the suture.

FIG. 14D shows a surgical suture/needle set package with a vibrant coating.

DETAILED DESCRIPTION OF THE INVENTION

Figure 1:
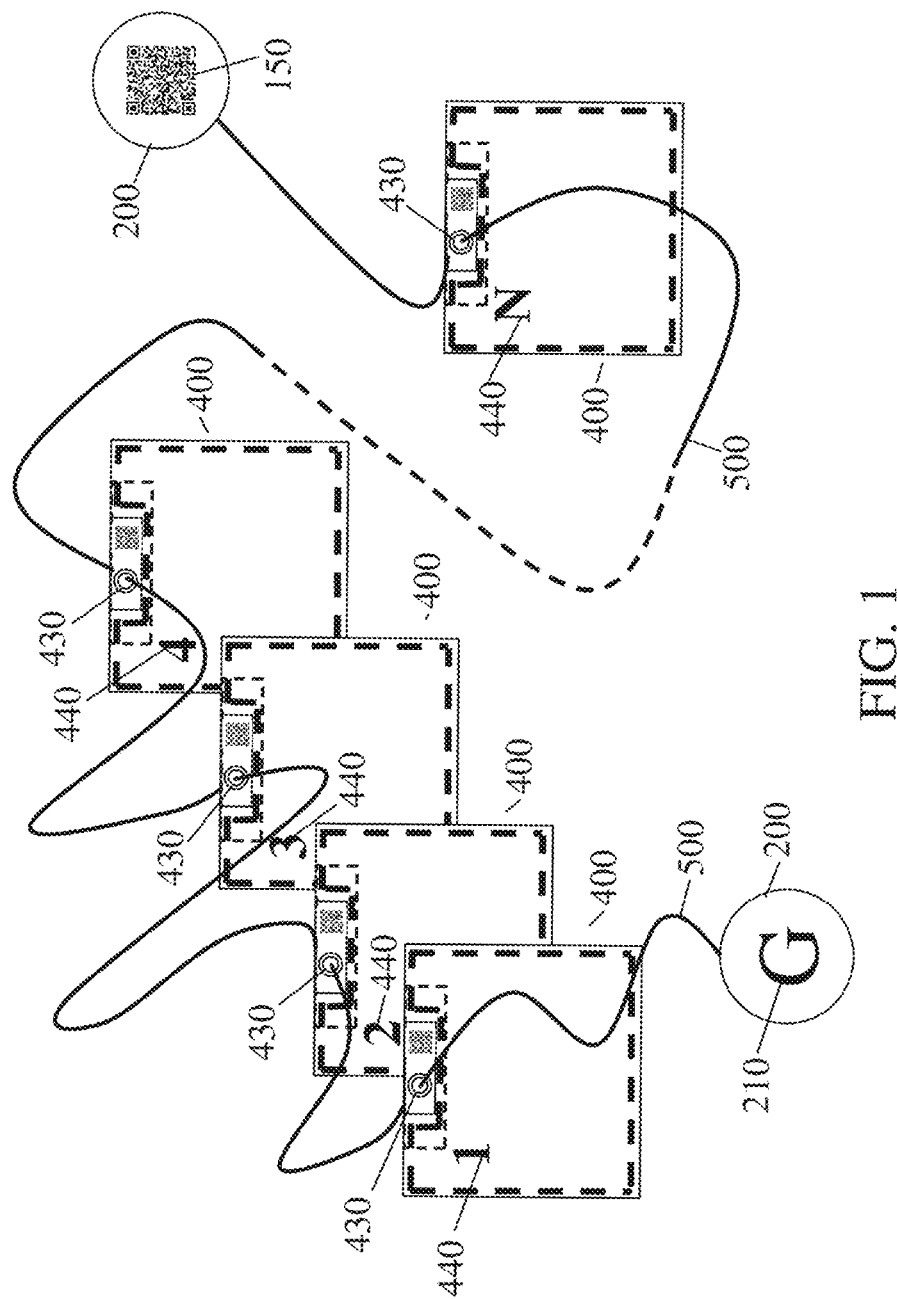
FIG. 1 shows a plurality of surgical sponges connected by a stringer.

A stringer system generally includes a stringer that can be combined with a variety of surgical objects. In some embodiments, the stringer is connected to surgical objects through permanent apertures existing in the surgical object. In other embodiments, the stringer is connected to surgical objects through the addition of a variety of removable retainers that can be attached to surgical objects and also provide an aperture through which the stringer can be threaded. In both embodiments, the stringer provides a slidable physical connection between a plurality of surgical objects. In other embodiments, a single surgical object is connected, via an aperture in the instrument or a retainer, to a tracking tag with a stringer forming a lanyard.

In all stringer embodiments, the connection between surgical objects via the stringer, established either prior to introduction to the surgical field or during the surgical procedure, guarantees the removal of all objects after they are no longer needed in the surgical field. The surgeon need only fix one or both ends of the stringer outside the surgical field, using tapes or clamps, for example, and then follow the course of the stringer through the surgical field to retrieve surgical objects that have been connected to it.

This physical connection is particularly useful with surgical sponges, gauzes and other absorbent pads (henceforth generally referred to as "sponges" or "pads") that may be difficult to identify when soaked with blood. Similarly, small clamps and other surgical instruments, whether used singly or in multiples, may become obscured behind internal organs and escape visual detection, and even manual palpation in some cases, prior to closure of the surgical field.

The term "stringer" is used herein in reference to a stringer forming a physical connection between multiple surgical objects, and also embodiments where the stringer forms a lanyard used to localize a single surgical object.

In some embodiments, the devices and methods described herein localize and track surgical objects through application of a vibrant coating. While these surgical objects are discussed within the context of human surgery, it is understood that the same surgical objects also have applications within veterinary medicine and the embodiments discussed herein are equally applied in that context. These objects include surgical instruments, including but not limited to, forceps, surgical clamps and occluders of various design, scalpels, retractors, mechanical cutters, chisels, suction tips and tubes, calipers, surgical needles, and any instrument that may be used in the body during a surgical procedure. Such instruments are often manufactured from stainless steel, but may alternatively or additionally be constructed of synthetic materials such as Polyetherimide (PEI), Polycarbonate (PC), Polysulfone (PS), and others.

In other embodiments, vibrant coatings are added to surgical objects such as absorbent and non-absorbent surgical sponges, and gauzes. The sponges and/or gauzes may be manufactured from cotton, rayon, polyester, Telfa® fibers, polyvinyl acetal, polyurethane, cellulose, micro cellulose, other natural and synthetic fibers, foams, woven and non-woven textiles and other materials. These surgical objects are referred to as "pads" or "sponges" herein. In other embodiments surgical objects such as surgical sutures have a vibrant coating applied. These sutures may be made of catgut, chromic catgut, polyglycolide (PGA), polydioxanone (PDS) or other materials.

The coatings preferably include vibrant colors that are easily visible to the unaided human eye. The colors are preferably chosen to contrast with the colors of physiological structures in the human body. Some examples of vibrant colors include, but are not limited to, bright neon colors, colors not occurring often in nature, and others. The vibrant coatings are preferably nontoxic, biocompatible, and hypoallergenic. In preferred embodiments, the vibrant coatings are also non-leaching. For the purpose of this description, a vibrant coating refers to a discrete layer of a substrate containing bright, easily viewable pigments (either by the naked eye or with instrumentation) applied to an existing surface, through dipping, spraying, anodizing, powder coating, application of vitreous or non-vitreous ceramics, porcelain, glass, epoxy and other resins, or other external means. This definition also includes application of pigments directly in the production of plastics, textiles, foams, and other natural and synthetic materials used in the manufacture of surgical objects such that pigments form a vibrant coating on the surface of the finished device.

While the term "coating" is used throughout this application, in some embodiments, the vibrant coloring is included within the instrument or object itself, preferably during the manufacture of the instrument or object. For example, the vibrant coloring may be added to plastics used to make surgical instruments, during a molding process. As another example, the vibrant coloring is mixed with a gauze or sponge material to create an amalgamation used to make the finished gauze or sponge. Any manufacturing process for the instrument or surgical object that is able to incorporate coloring or pigment may be used.

In some preferred embodiments, the vibrant coatings alternatively or additionally include one or more photo-reactive coatings. For the purpose of this description, a photo-reactive coating refers to a discrete layer of a substrate containing photo-reactive pigments applied to an existing surface, through dipping, spraying, anodizing, powder coating, application of vitreous or non-vitreous ceramics, porcelain, glass, epoxy and other resins, or other external means. This definition also includes photo-reactive pigments applied directly in the production of plastics, textiles, foams, and other natural and synthetic materials used in the manufacture of surgical objects such that pigments form a coating on the surface of the finished device.

In these embodiments, a photo-reactive pigment is understood to be a pigment which is fluorescent and/or phosphorescent, being highly reflective at a given bandwidth or combination of bandwidths of light when exposed to broad spectrum light, narrow spectrum light, or emitting light at a given bandwidth or group of bandwidths for at least a period of time when external sources of light are removed.

In some preferred embodiments, a number of photo-reactive pigments are used that fluoresce when exposed to light in the wavelength range of 345-375 nm, and preferably at a wavelength of 365 nm (black light), and are also highly visible when exposed to broad spectrum white light. Such pigments are available in colors including red, purple, orange, yellow, green, blue and pink, among others. In another embodiment, phosphorescent photo-reactive pigments ("glow in the dark") are used that are available in a wide range of colors such as green, blue, purple, orange, yellow, and pink, among others. These pigments also possess the quality of being highly visible under white light exposure, and are incorporated in a wide variety of substrates and materials including acrylics, plastics, epoxy and other resins, vitreous and non-vitreous ceramics, porcelain, glass, and others, alternatively, or in addition to, fluorescent pigments.

The likelihood of leaving a surgical object in the patient is significantly reduced due to the intense vibrant coloration of the vibrant coating. Even when covered with blood or other bodily fluids, such vibrant colors contrast strongly with colors naturally occurring in the human body, making them difficult to overlook. Particularly when UV-A or other fluorescent or phosphorescent vibrant coatings are used, only a small portion of a surgical object need be exposed to a narrow-band spectral source during a pre-closing scan to make its presence evident. This is particularly useful in abdominal surgery where, for example, a clamp may become obscured by bowel or other internal organs and missed by a simple visual scan or even manual palpation.

In additional embodiments, tracking tags are added to surgical objects to assist in their identification and localization in the surgical field. These tracking tags are removably attached to a complete range of surgical objects. These tracking tags also make use of the vibrant coatings described herein.

In even further embodiments, instrument specific peel and stick labels, and peel and stick labels for sponges, gauzes, and other types of surgical pads and other surgical objects, such as sutures, are generated and posted on a board during the surgical procedure. In these embodiments, when each surgical object is taken out of service and definitively accounted for, its respective label is preferably relocated to a separate section on the board.

Human readable characters and computer readable optical codes are utilized in various embodiments on tracking tags and instruments to more definitively track individual surgical objects pre- and post-surgery. In some preferred embodiments, human readable characters and/or computer readable codes are applied to surgical objects in a second vibrant coating that contrasts with the vibrant coating on the surgical object. In other preferred embodiments, human readable characters and/or computer readable codes are etched, engraved, stamped, or otherwise formed as surface voids in the surgical object that are then preferably filled with a second vibrant coating that contrasts with the vibrant coating on the surface of the surgical object.

Reinforcement layers incorporated into gauzes, sponges, and other surgical pads further facilitate labeling with computer readable optical codes. Reinforcement layers having grommets, eyelets, hollow rivets or other perforation reinforcements affixed to them provide fixation points for tracking tags similar to those used with surgical instruments, and also allow multiple pads to be strung together in groups that are used in the same location at the same time. In some preferred embodiments, these reinforcement layers have a second vibrant coat that contrasts with the vibrant coat of the rest of the surgical pad.

Referring now to FIG. 1, a stringer 500 is shown with connection to a plurality of surgical sponges 400. The stringer 500 may be formed from materials including, but not limited to, polymer filaments (e.g., polyetherimide, polycarbonate, or polysulfone), stainless steel wire, artificial or natural fibers forming a cord, or other materials that are bio-compatible and capable of being formed into a flexible line, thread, or cord that can be brought into a sterile state. Preferably, these materials are also capable of being coated with a vibrant and/or spectrum-specific photo-reactive pigment, or having such a pigment added to its material of manufacture.

FIG. 1 shows a plurality of surgical pads 400 on a stringer 500 passing through grommets 430, metallic or synthetic eyelets, hollow rivets, or other perforation reinforcements on each pad 400. Tracking tags 200 at each end of the stringer 500 keep the pads 400 in place on the stringer 500. Since it is common to use numerous pads 400 as packing in some surgical or trauma cases, this system provides for individual pads 400 being freely placed in the body cavity or wound site, while ensuring that they can be removed without any being overlooked. For example, a pre-packaged set of pads 400 may contain 10 pads 400 on one stringer 500.

In some embodiments, the pads 400 are imprinted with human readable characters 440 indicating lot number, pad number, and/or other tracking information. Human readable characters 440 are preferably applied using a vibrant color that contrasts with the vibrant coating used throughout the rest of the pad 400. Alternatively or additionally, as shown in FIG. 8A, computer readable codes 150 may be applied to a reinforcing layer 410 to provide for computer assisted logging of pads 400. Human readable characters 440 and computer readable codes 150 are applied to only one side of the surgical pad 400 and/or reinforcing layer 410 in some embodiments, while in other embodiments they are applied to both sides of the pad 400 and/or reinforcing layer 410.

Figure 21:
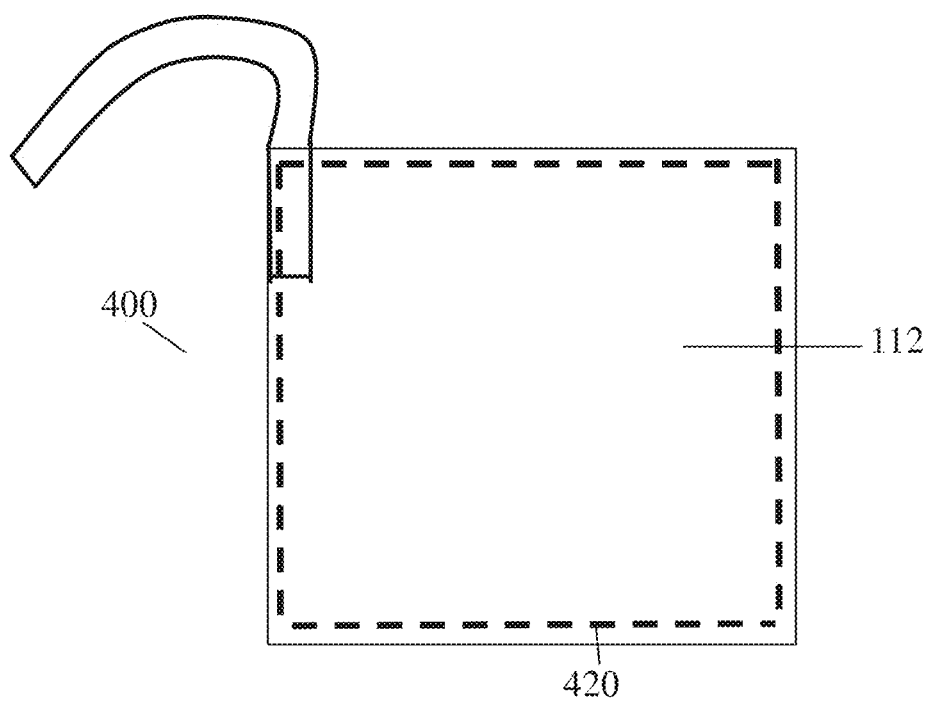
FIG. 21 shows a generalized surgical pad having a high visibility coating applied to it.

FIG. 21 shows a generalized surgical pad 400 and represents any of a variety of medical and surgical disposable items, including, but not limited to, gauze pads, absorbent surgical sponges, and non-absorbent surgical sponges. Such pads are made of Telfa® material, cotton, rayon, polyester, polyvinyl acetal, polyurethane, cellulose, microcellulose and other natural and synthetic fibers, foams, and woven or non-woven textiles and fabrics. In FIG. 21, a simple gauze sponge pad 400 having stitching 420 about its perimeter is used for illustrative purposes. A vibrant coating 112 has been applied to the surface of the pad using a non-leaching color-fast dye in one preferred embodiment. In another preferred embodiment, a vibrant coating 112 has been created by adding pigments described herein during the manufacture of the fibers used to form the pad, as in the case of synthetic fibers for example. In a third preferred embodiment, a vibrant coating 112 has been created by adding vibrant pigments described herein directly to the components used to create foam (e.g., polyvinyl acetal, polyurethane, or other medical foam) in the case of a foam pad.

In some embodiments shown in FIG. 21, fluorescent, phosphorescent, UV-A sensitive or other spectrum selective photo-reactive pigments are also, or alternatively, added to the vibrant coating 112. Vibrant coatings 112 may also be applied to the pads 400 shown in FIG. 1.

In one embodiment, sponges 400 are pre-strung on a stringer 500 during manufacture and packaging. This embodiment is directed toward field trauma and surgical applications where large numbers of sponges are applied to a wound or within a surgical field as packing. This embodiment, as will be discussed in more detail herein, is of particular value in trauma situations in which first responders or medics may place a large number of surgical objects, such as sponges, in a patient and then transfer that patient to a hospital where staff may not be aware of what, and how many, objects have been applied. Having those objects physically connected and traceable from one end of the stringer 500 to the other ensures that imperfect communications between first responders and hospital staff does not result in objects being left in the patient. This embodiment is also useful in any application where a large number of sponges 400 are needed.

Figure 2A:
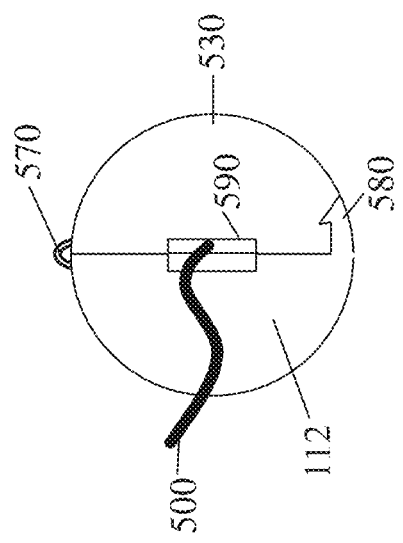
FIG. 2A shows a top view of a spherical tracking tag removably connected to a stringer.
Figure 3A:
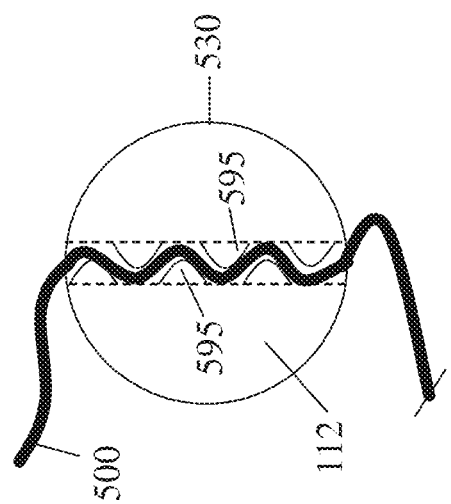
FIG. 3A shows a top view of an alternate embodiment of a spherical tracking tag removably connected to a stringer.
Figure 2B:
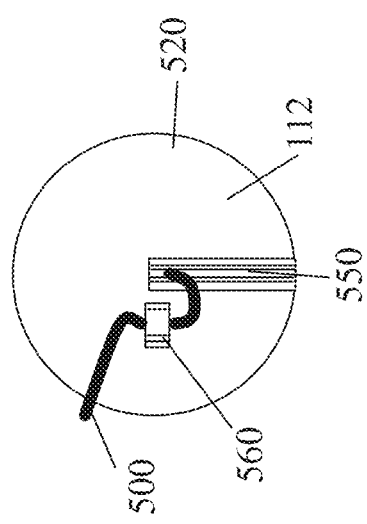
FIG. 2B shows a side view of a spherical tracking tag removably connected to a stringer.
Figure 3B:
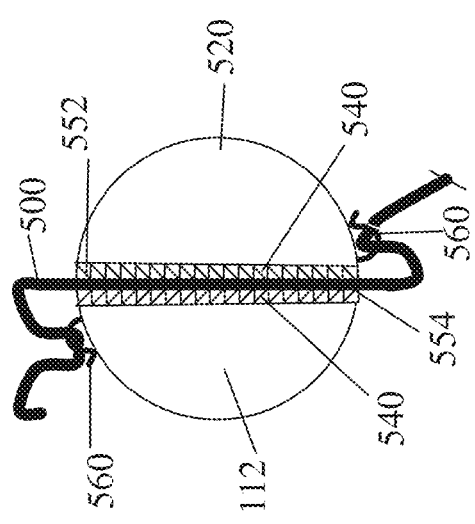
FIG. 3B shows a cross-sectional side view of an alternate embodiment of a spherical tracking tag removably connected to a stringer.

In other embodiments, less than the full number of pads 400, or other surgical objects, pre-packaged on a stringer 500 may be used in a particular setting, and one or more additional stringer 500 terminators 520, 530, shown in FIGS. 2A 3B, are also preferably included. Thus, once the required number of pads 400 are inserted in the body, the stringer 500 is cut, and a terminator 520, 530 is added to the free end of the stringer 500 running through the grommets 430, eyelets, hollow rivets or other perforation reinforcements of the pads 400 already in the body. Consequently, the integrity of the pad 400 set is maintained.

At each end of the stringer 500 is a tracking tag 200. Tracking tags 200 serve multiple functions. The tracking tags 200 first serve as keepers that prevent the stringer 500 from sliding out of apertures, created by reinforced grommets 430 in this embodiment, on sponges 400, other surgical objects, or surgical object retainers. Secondly, tracking tags 200 form a substantial element that is not only visually obvious, but also may be affixed to the patient or surgical drape with tape or other methods. Tracking tags 200 also provide a surface area for placement of various computer readable or human readable indicia 150, 210 that may be useful in tracking surgical objects connected by the stringer 500. Indicia may be applied during manufacture of a stringer 500 system, or by the end-user via peel-and-stick labels, permanent marker, or any method that effectively applies the indicia 440. Indicia 440 may also be placed on sponges 400 to provide additional information, for example, a sequential numbering of sponges 400 pre-packaged on a stringer 500.

Tracking tags 200 may be attached to the ends of a stringer 500 connecting a number of surgical objects at the point of manufacture, for example, when a large number of sponges 400 are pre-packaged with a stringer 500 connecting them. However, in some situations, not all of the pre-packaged sponges 400 will be needed at the same time, or in one procedure. In these situations, the stringer 500 may be simply cut at an appropriate point, and a removable tracking tag 520, 530, shown in FIGS. 2A-3B, may be applied to the cut end of the stringer 500 to maintain the integrity of the stringer 500 system.

While the stringer 500 system and the tracking tags 200, 520, 530 it includes has been discussed thus far in the context of a pre-packaged set of surgical objects, the stringer 500 and tracking tags 520, 530 may also be made available as individual components. Thus, stringers 500 of convenient length may be individually assembled and customized by healthcare practitioners whenever needed, for example, during preparation of surgical trays, during a surgical procedure, or during a first responder call.

Referring now to FIGS. 2A-3B, spherical removable tracking tags 520, 530 are shown in more detail. FIGS. 2A-2B show a spherical removable tracking tag 520 having a channel 550, narrower at one end 554 than the other end 552, formed in it. The channel 550 is also preferably lined with serrations 540, or other surface features, that grip the stringer 500 as it is first laid into the wide end 552 of the channel 550, and then pulled firmly down into the narrow end 554 of the channel 550, firmly gripping the stringer 500. In some embodiments, spring loops 560, or other similar elements, are added near the channel 550 to stabilize the stringer 500 where it exits the channel 550 on either side of the removable tracking tag 520.

In another embodiment, shown in FIGS. 3A-3B, a snap-lock removable tracking tag 530 is used. The snap-lock removable tracking tag 530 is formed in two halves having a hinge 570 holding them together. The stringer 500 need only be placed in a channel 590 formed in the center of one or both halves of the snap-lock tracking tag 530, and the two halves closed around it. A latch 580, snaps, or other locking structure keeps the removable tracking tag 530 closed after placement of the stringer 500. Mating teeth 595, or other surface features formed inside the channel 590, grip the stringer 500 when the snap-lock removable tracking tag 530 is closed.

A vibrant coating 112, described herein, is also preferably applied to the removable tracking tags 520, 530, and includes a vibrant colored pigment that highly contrasts with physiological structures. In other embodiments, the vibrant coating 112 may, alternatively or additionally, include pigments that are photo-reactive in the range of 345-375 nm.

The fixed tracking tags 200 of FIG. 1, and the removable tracking tags 520 and 530 of FIGS. 2A-3B, have been shown as simple spheres. However, tracking tags 200, 520, 530 may have any three dimensional shape such as disks, cubes, plates, or other forms, have various dimensions and use various attachment mechanisms.

A variety of indicia may also be placed on the tracking tags 200, 520, 530 including, but not limited to, human readable characters 210 (FIG. 1) and computer readable indicia (e.g., Q-codes 150, FIG. 1). When the stringer 500 system is manufactured and packaged with surgical objects, these indicia 210, 150 may also be included on product packaging, for example in the form of peel-and-stick labels, and also on tracking tags 200, 520, 530, to identify the surgical objects connected by the stringer 500.

Figure 4:
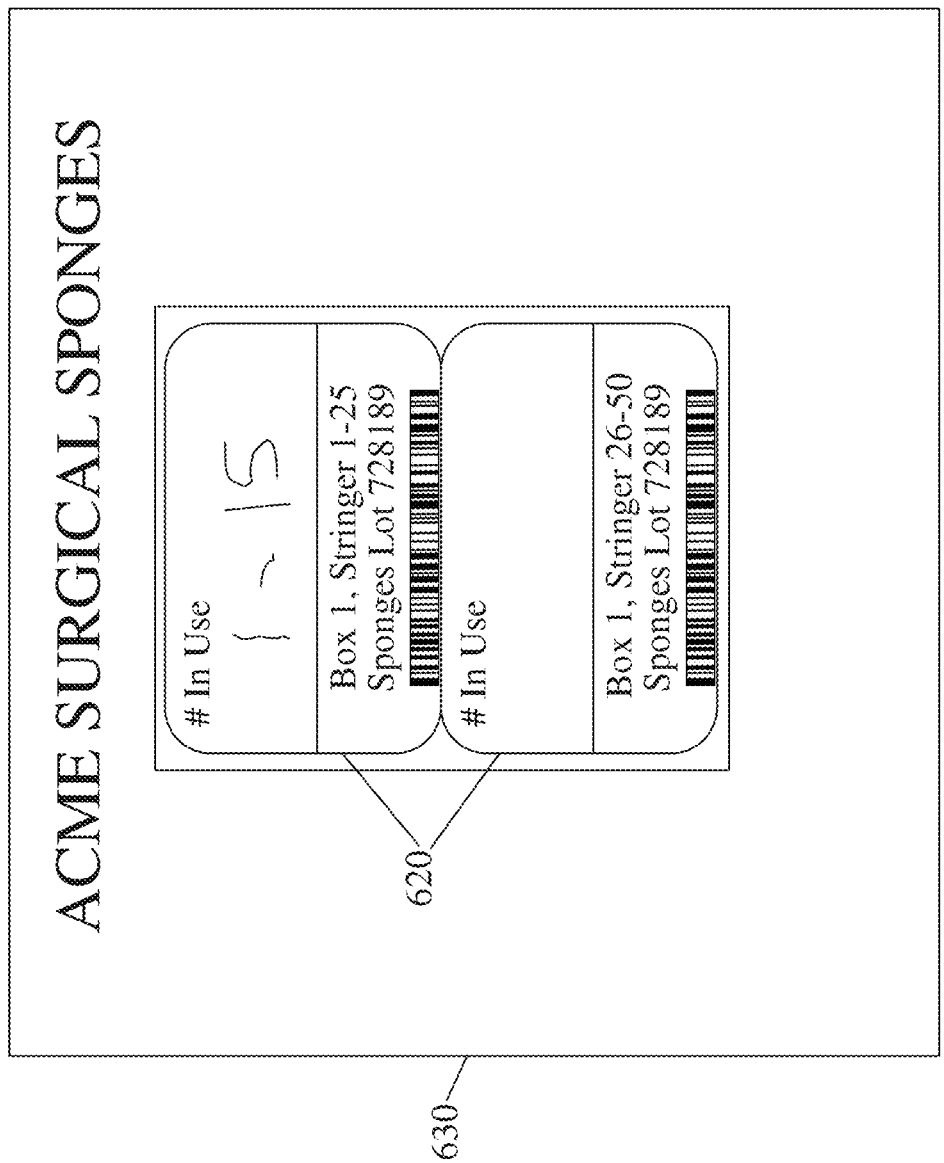
FIG. 4 shows packaging for a pre-manufactured stringer system connecting surgical objects, including peel-and-stick labels with indicia identifying the surgical objects on each stringer in the package.

In one embodiment, shown in FIG. 4, a number of sponges 400 are pre-packaged on stringers in one package 630, with peel-and-stick labels 620 affixed to the outside of the package 630, and/or inside the package in sterile enclosures protecting the stringers 500 and sponges 400 attached thereto. Peel-and-stick labels 620 may also include space for surgical staff to add notations as necessary, for example, when less than the full number of sponges 400 on a pre-packaged stringer is actually used.

For example, as shown in FIG. 4, a box 630 of pads 400 contains two stringers 500 each having 25 individually numbered pads 400 associated with it. The box 630 includes two peel and stick labels 620, one for each stringer 500. Each peel and stick label indicates the pad 400 numbers on a stringer 500, 1-25 and 26-50 in the example shown, as well as other lot information for that box 630. Space is also provided for surgical personnel to indicate which pads 400 on a stringer 500 have been used. In this example, pads 400 one through fifteen (1-15) are in use from the first stringer 500 in the box 630.

Figure 5:
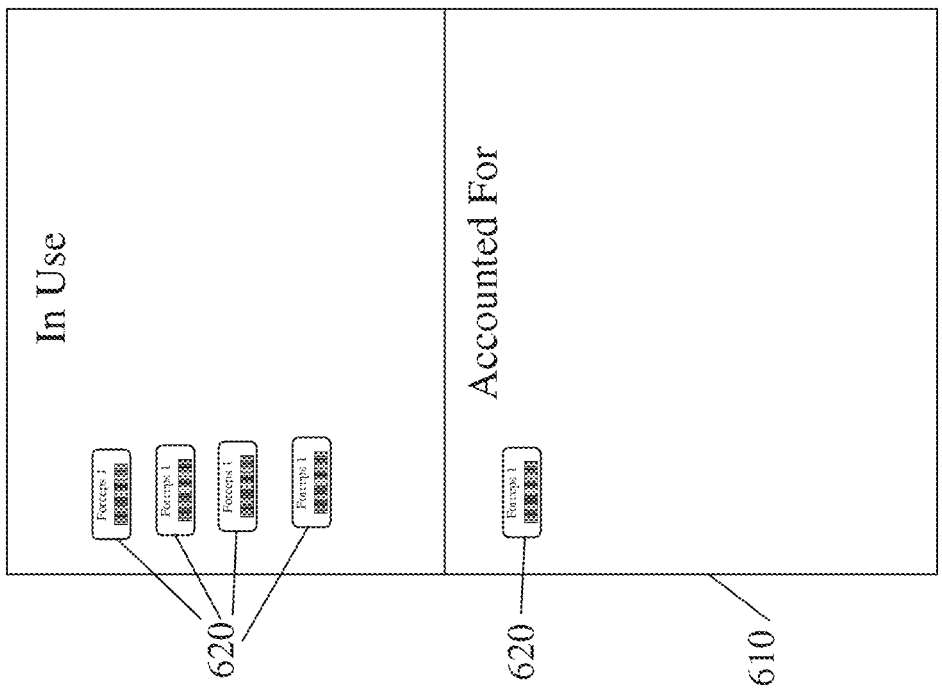
FIG. 5 shows a tote board for application of peel-and-stick labels, with an "In Use" and "Accounted For" section. The tote board and labels may be used in combination with the stringer system.

When pre-packaged sponges 400 are put to use, the peel-and-stick labels 620 associated with them may be moved to a log list, such as in a clipboard, log book, or (as shown in FIG. 5) a tote board 610. Positioning the peel-and-stick labels 620 according to the status ("In Use", "Accounted For") of the surgical objects being tracked thus allows for real time manual tracking of the surgical objects.

Figure 6:
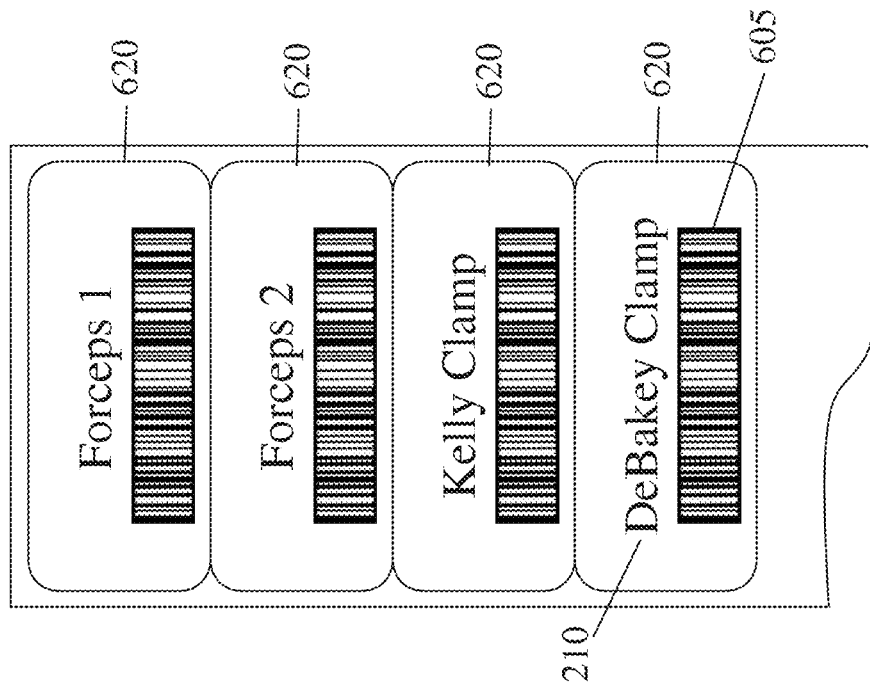
FIG. 6 shows user generated peel-and-stick labels. In some embodiments, these labels can be applied to tracking tags of the stringer system, and the tote board of the stringer system.

When custom stringers 500 are created for a specific surgery, as shown in FIG. 6, customized peel-and-stick labels 620 may also, or alternatively, be printed. As with peel-and-stick labels 620 created for pre-packaged surgical objects, peel-and-stick labels 620 created for custom stringer 500 systems may contain human readable characters 210, computer readable characters (e.g., Q-codes 150, bar codes 605), or a combination thereof. Duplicate peel-and-stick labels 620 may be created at the same time for placement on the stringer 500 tracking tags 200, 520, 530 to assist in the tracking process. Both types of labels 620 may also be provided with space for medical practitioners to make notations that can be added to manual or computerized tracking logs, or modified during surgery, to note the addition or removal of surgical objects to or from the stringer 500 system. While clamp names are used on the labels 620 in FIG. 6, in other embodiments, the instruments 100 may be labeled in another manner, for example as "I1", "I2", "I3", etc.

In one preferred embodiment, vibrant coatings 112 are added to the stringer 500 system including any or all of the stringers 500, tracking tags 200, 520, 530, peel-and-stick labels 620, sponges 400, surgical instruments 100, or any combination thereof. The vibrant coatings 112 preferably include vibrant colors that are easily visible to the unaided human eye and not normally found in anatomical structures or bodily fluids. The colors are thus chosen to contrast with the colors of physiological structures in the human body. Some examples of vibrant colors include, but are not limited to, bright neon colors and colors not occurring often in nature. The vibrant coatings are preferably nontoxic, biocompatible, hypoallergenic and non-leaching.

For the purpose of this description, a vibrant coating 112 refers to a discrete layer of a substrate containing bright, easily viewable pigments (either by the naked eye or with instrumentation) applied to an existing surface, through dipping, spraying, anodizing, powder coating, application of vitreous or non-vitreous ceramics, porcelain, glass, epoxy and other resins, or other external means. This definition also includes application of appropriate pigments, described herein, directly in the production of plastics, textiles, foams, and other natural and synthetic materials used in the manufacture of a surgical object such that the pigments form a vibrant coating 112 on the external surface of the finished device.

Hence, while the term "coating" is used throughout herein, in some embodiments the vibrant coloring is included within the elements of the stringer 500 system, preferably being incorporated during their manufacture. For example, the vibrant coloring may be added to plastics used to make the tracking tags 200, 520, 530 during a molding process. However, any manufacturing process that is able to incorporate coloring or pigment may be used.

In some embodiments, the vibrant coatings 112 alternatively, or additionally, are photo-reactive through addition of photo-reactive pigments. In these photo-reactive embodiments, a photo-reactive pigment is understood to be a pigment which is highly reflective at a given frequency, bandwidth, or combination of bandwidths of light when exposed to broad spectrum white light or spectrum-specific light. A photo-reactive pigment is understood to be phosphorescent when emitting light at a given frequency, bandwidth, or combination of bandwidths of light for at least a period of time when external sources of light are removed.

In one preferred embodiment, a number of photo-reactive pigments are used that fluoresce when exposed to light at wavelengths in the range of 345-375 nm, and are also highly visible when exposed to broad spectrum white light. Such pigments are available in colors including, but not limited to, red, purple, orange, yellow, green, blue, and pink.

The range of 345-375 nm is selected for a number of reasons. These wavelengths are highly visible in broad spectrum white light produced by surgical lamps commonly use in medical settings, daylight field conditions, and similar ambient lighting environments.

Further, transmission optical filters are available in this wavelength range and may be constructed using colored glass, high transmission colored-glass alternative filters having thin-film optical coatings, spectral separation elements, and similar technologies.

Figure 11B:
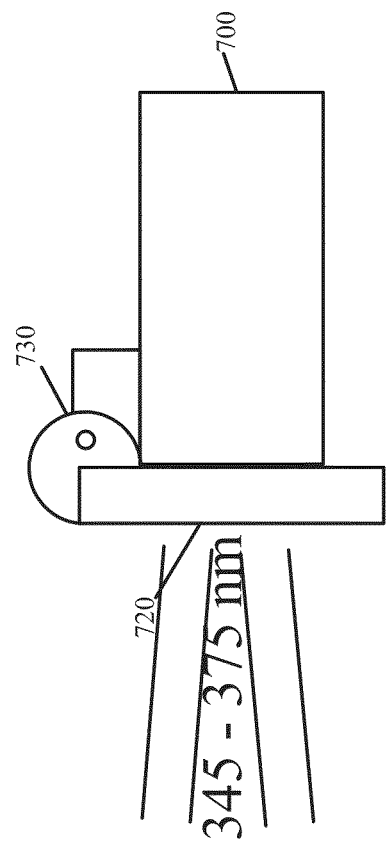
FIG. 11B shows a generalized surgical illuminator with a spectrum-specific filter attached and positioned in the illumination pathway.
Figure 11A:
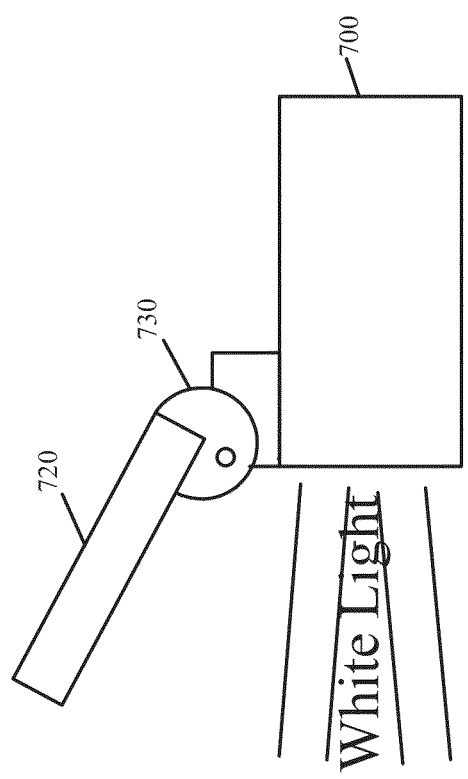
FIG. 11A shows a generalized surgical illuminator with a spectrum-specific filter attached and positioned outside the illumination pathway.

As shown in FIG. 11A, a transmission optical filter 720 in the range of 345-375 nm may be used in conjunction with a generic light source 700, such as fiber optically driven head lamps used by surgeons, or a dedicated hand-held battery powered illuminator. Through a hinge mechanism 730, the filter 720 may be moved away from the light source 700 if white light is desired (FIG. 11A), or flipped down into the light path when spectrum-specific illumination is desired (FIG. 11B). In the case of fiber optically driven head lamps, the filter 720 may be moved into and out of the path of light at the primary light source, before light enters the fiber optic pathway.

In alternate embodiments, spectrum-specific LEDs are employed without additional filtration as a low cost and simple component with which illuminators may be constructed. As such, in contrast to purely phosphorescent pigments, even under normal background light conditions, the stringer 500 system can be further visually enhanced to the naked eye by applying a light source 700 fitted with a transmission optical filter 720.

Figure 12A:
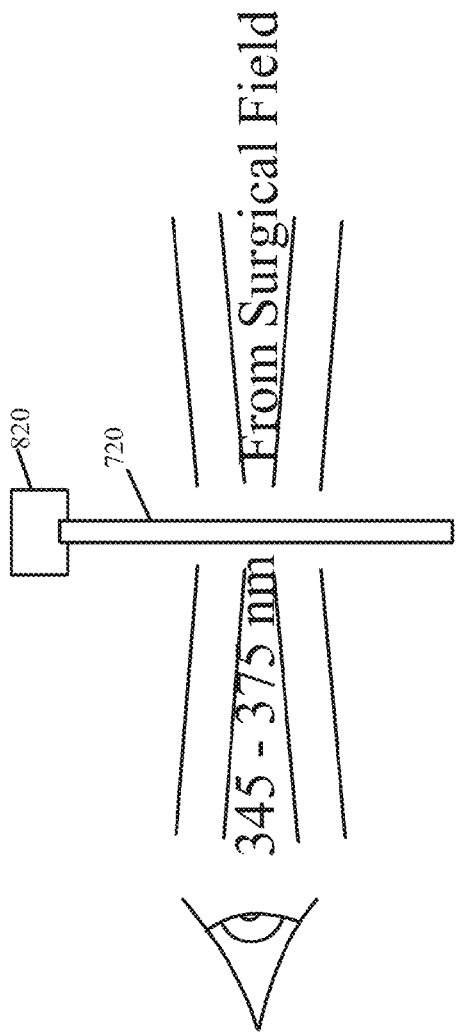
FIG. 12A shows a cross section of a spectrum specific filter fitted into eyeglass frames.
Figure 12B:
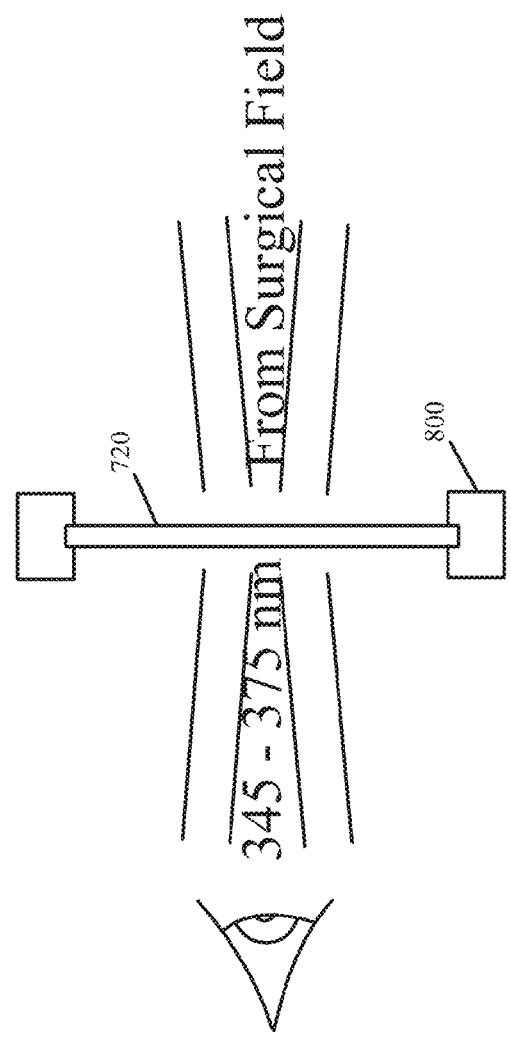
FIG. 12B shows a cross section of a spectrum specific filter fitted into goggle frames.

In addition, or as an alternative, as shown in FIG. 12A-12B, transmission optical filters 720 may be worn in front of the eyes of a person viewing the surgical field. For example, transmission optical filters 720 may be incorporated into eyeglass frames 800 (FIG. 12A) or goggle frames 820 (FIG. 12B), to filter out unwanted wavelengths of light and only allow light in the specified range to reach the eye.

Whether illuminators, wearable transmission optical filters 800, 820, or a combination of both are employed, is it not necessary to turn conventional ambient lighting off to obtain additional visual enhancement of the stringer 500 system. This is advantageous for other personnel in a surgery who may still need full ambient light conditions to perform their assigned tasks.

In another embodiment, phosphorescent photo-reactive pigments ("glow in the dark") are used that are available in a wide range of colors including, but not limited to, green, blue, purple, orange, yellow, and pink. These pigments also possess the quality of being highly visible under white light exposure, and are incorporated in a wide variety of substrates and materials including, but not limited to, acrylics, plastics, epoxy and other resins, vitreous and non-vitreous ceramics, porcelain, or glass, alternatively, or in addition to, fluorescent pigments. As described herein, phosphorescent photo-reactive pigments may be added in addition to, or alternatively to, vibrant pigments and fluorescent pigments in any of the embodiments described herein.

The stringer 500 system has heretofore been primarily discussed in conjunction with simple surgical sponges 400. As shown in FIG. 1, the stringer 500 may pass through a plurality of sponges 400, each of which has a grommet 430 creating a reinforced aperture in the sponge 400 through which the stringer 500 may pass, while also allowing the sponges 400 to freely slide along the length of the stringer 500.

Figure 7:
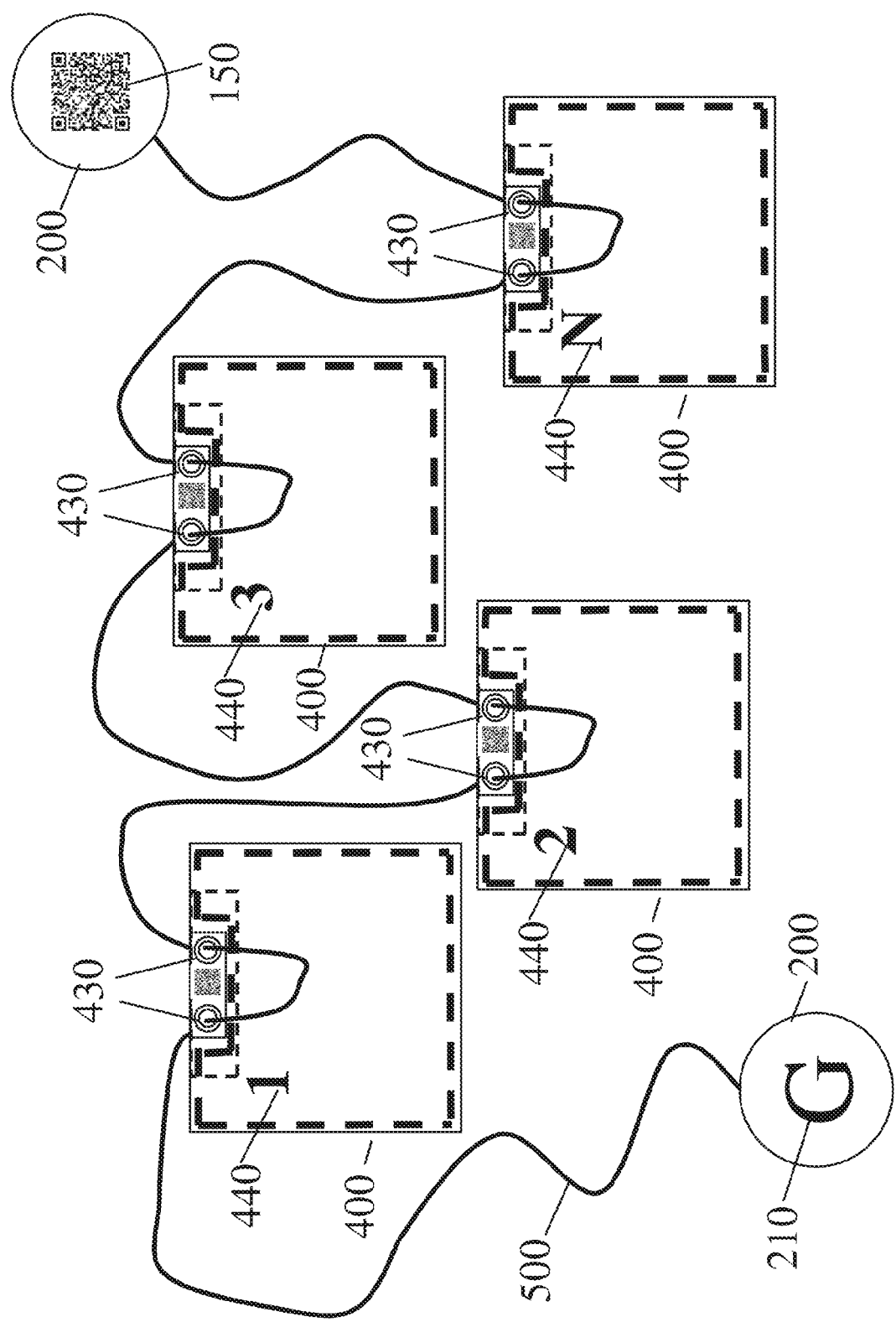
FIG. 7 shows a stringer system connecting a plurality of surgical sponges having multiple apertures through which the stringer is threaded.

In another embodiment, as shown in FIG. 7, sponges 400, or other surgical objects, may be provided with two or more grommets 430 through which the stringer 500 may pass. In this embodiment, the sponges 400 are not only held in an orientation in which their plane is substantially parallel to the stringer 500 when the stringer 500 is outstretched, but the sponges 400 have greater resistance to sliding along the stringer 500.

This configuration is advantageous as it precludes the sponges 400 from bunching or sticking together. Thus, individual placement of the sponges 400 in the surgical field is easier, and by pulling the two ends of the stringer 500 apart after removal from the surgical field, the sponges 400 are also automatically separated from one another to make counting and verification of their retrieval more straightforward.

As also shown in FIG. 1 and FIG. 7, sponges 400 may be specifically constructed for use with the stringer 500 system described herein. In one embodiment, indicia 440 are applied to each sponge 400, for example, to uniquely number each sponge 400 on a stringer 500 connecting "N" sponges 400. Sponges 400 may be manufactured with vibrant colors as described herein and applied to the stringer 500 system. Vibrant coloration may be uniformly applied to all sponges 400 on a single stringer 500, or other schema may be applied, for example, applying one vibrant color to even numbered sponges 400 and a different color to odd numbered sponges 400. Varying application of vibrant colors provides a further optical differentiation feature, as holding a used stringer 500 of sponges 400 outstretched will immediately make a missing color in the alternating pattern along the stringer 500 apparent.

Figure 8I:
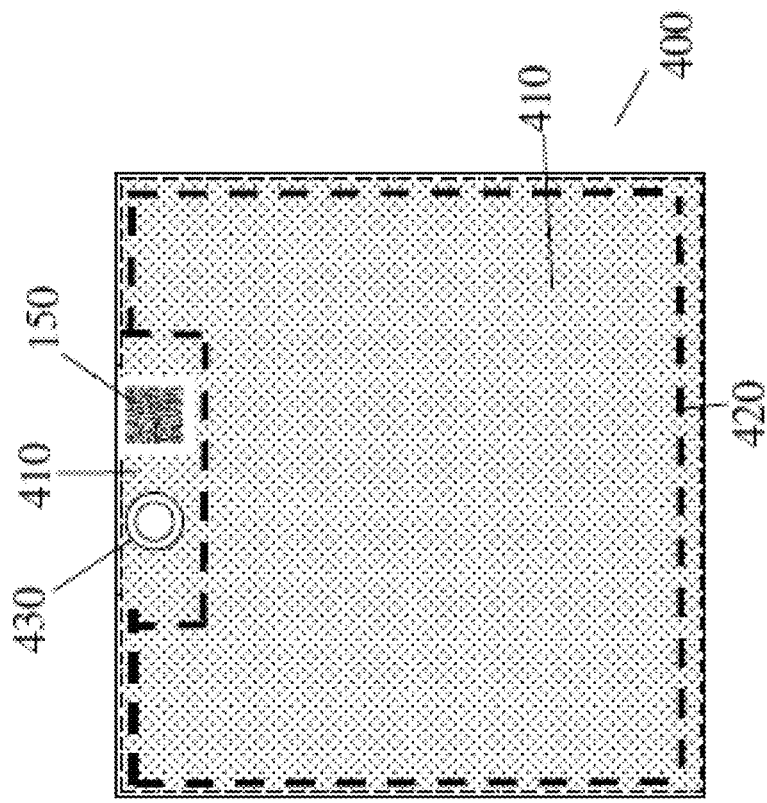
FIG. 8I shows a surgical sponge with a reinforcement layer throughout the entire pad, and having a grommet aperture.

In some embodiments, as shown in FIG. 8A-8J, sponges 400 are constructed with one or more reinforcement layers 410. In FIGS. 8A-8B, the reinforcement layers 410 may be secured on the exterior of, or within, the sponge 400 structure using stitching 420 around the outer perimeter of the sponge 400, adhesives, or through direct integration into the sponge 400 material during manufacture in the case of foam based sponges 400. In other embodiments, the reinforcing layer 410 is attached using other mechanisms including, but not limited to, medical grade glue, ultrasonic welding, or other methods compatible with both the materials used, and the surgical environment. In preferred embodiments, the sponges 400 are used with the stringer 500 system described herein.

In addition to providing structural support to the grommet 430 that reinforces apertures for the stringer system 500, exposed sections of the reinforcement layer 410 may also have indicia 150 applied to them, such as human readable characters 440 and computer readable characters 210, 150 that may assist in the tracking process. In this embodiment, the grommet 430 is made from a biocompatible material such as polypropylene, polyetheretherketone, polysulfone, polycarbonate, latex, vinyl, nitrile rubber, or another biocompatible material, and is incorporated to provide for attachment of a tracking tag 200 stringer 500 as described herein. While a grommet 430 is shown in FIGS. 8A-8J, a synthetic or metallic eyelet, hollow rivet, or other perforation reinforcement is alternatively or also preferably used.

As shown in FIG. 8B, at least a portion of the reinforcing layer 410 is visible through, for example, a cut out in a portion of the sponge 400. A computer readable optical code, such as a Q code 150 or a bar code 605, on the reinforcing material 410 allows a computer assisted count of sponges 400 entered into the surgical procedure, and an accurate count of the sponges 400 removed from the patient as the reinforcing layers 410 are wiped clean and scanned at removal. Hence, a higher level of verification of retrieval of sponges 400 connected via a stringer 500 may be achieved.

FIG. 8C shows a cross-section of a two-ply sponge 400 having a reinforcing layer 410. The reinforcing layer 410 is inserted between two plies of the sponge 400, with a cut out in one ply. In other embodiments, a reinforcing layer 410 is directly applied to one external surface of a sponge 400 using stitching, ultrasonic welding, glues, or other medically acceptable methods. For sponges 400 constructed from synthetic foam or other synthetic materials, bulk sponge 400 material is slit on one or more sides during the manufacturing process, facilitating insertion and bonding of reinforcing layer 410 materials into the slit so formed.

FIG. 8D shows a detail of a reinforcing layer 412, in which the reinforcing layer 412 is a single uniform layer. In another embodiment, shown in FIG. 8E, two reinforcing layers 412, 414 form the reinforcing layer 410. In this embodiment, a first layer 412 is uniformly in continuous contact and fixed to a second layer 414. As one example, the first material 412 is Mylar® film or another thin plastic film or sheet, preferably with information imprinted it. In this example, the second layer 414 is preferably made of latex, neoprene, isoprene, nitrile rubber, or other material that provides additional strength, while still providing a high degree of flexibility that does not hinder the intended use of the sponge 400.

FIG. 8F shows a tri-layer reinforcing layer 410. In this embodiment, a first layer 412, for example, of plastic film, is bonded to a second layer 414, for example of isoprene, on one side, and a third layer 416, for example also of isoprene, on the other side.

Reinforcing layers 410 of more than three layers are also possible, and any of the materials described herein, or similar materials, may be used in different combinations in multi-layer reinforcing layers 410, any or all of which may have a vibrant coating 112 that, for example, matches or contrasts with the vibrant coating 112 of the sponge 400. In some embodiments shown in FIGS. 8A-4F, fluorescent, phosphorescent, UV-A sensitive or other spectrum selective photo-reactive pigments are also, or alternatively, added to the vibrant coating.

Figure 8J:
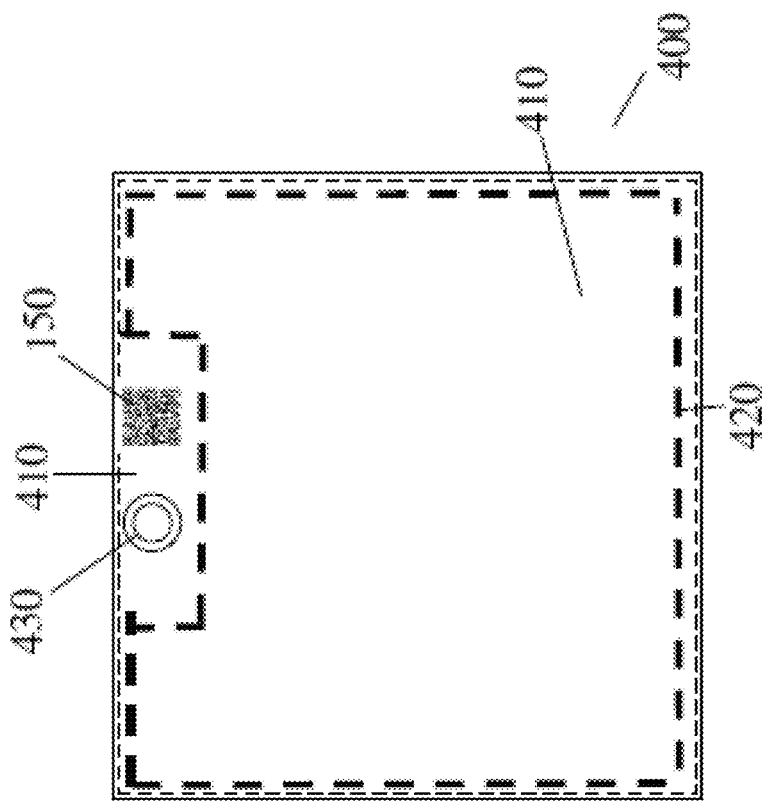
FIG. 8J shows a surgical sponge with a perforated reinforcement layer throughout the pad, and having a grommet aperture.

FIGS. 8A-8F show a reinforcing layer 410 (thin dashed lines in FIGS. 8A and 8B) that is limited in extent relative to the total area of the sponge 400. In other embodiments, as shown in FIG. 8G, the reinforcing layer 410 (thin dashed lines) is located on two edges of a sponge 400, or as shown in FIG. 8H, on the entire pad 400 perimeter (thin dashed lines). Alternatively, as shown in FIGS. 8I-8J, the reinforcing layer 410 may extend throughout the entire area of the pad 400, using either a solid or perforated reinforcing layer 410 material. In FIGS. 8I-8J, upper pad 400 layers have been removed from the diagram for clarity to show the reinforcing layer 410.

The embodiments shown in FIGS. 8I-8J have particular value in trauma applications in which a large wound is covered externally, and it is desirable for the covering to have more structure than is provided by a pad 400 of simple gauze, foam, or other construction.

In addition to coatings that include vibrant colored pigments, any or all of the individual elements of the embodiments shown in FIG. 8A-8J may additionally, or alternatively, include a vibrant coating 112 containing a pigment that is photo-reactive to specific frequencies of light, preferably in the range of 345-375 nm. Similarly, indicia present on any or all of these elements may be printed, or otherwise applied, with inks or substrates that also include vibrant colors or photo-reactive pigments described herein, or a combination thereof.

Heretofore, the stringer 500 tracking system has been discussed primarily in regard to surgical sponges 400 of various constructions. However, through the addition of retaining elements that include one or more apertures to accept the stringer 500, the stringer 500 system may also be applied to a variety of surgical instruments as well. Alternatively, the stringer 500 can be passed through existing apertures in surgical instruments.

Figure 9:
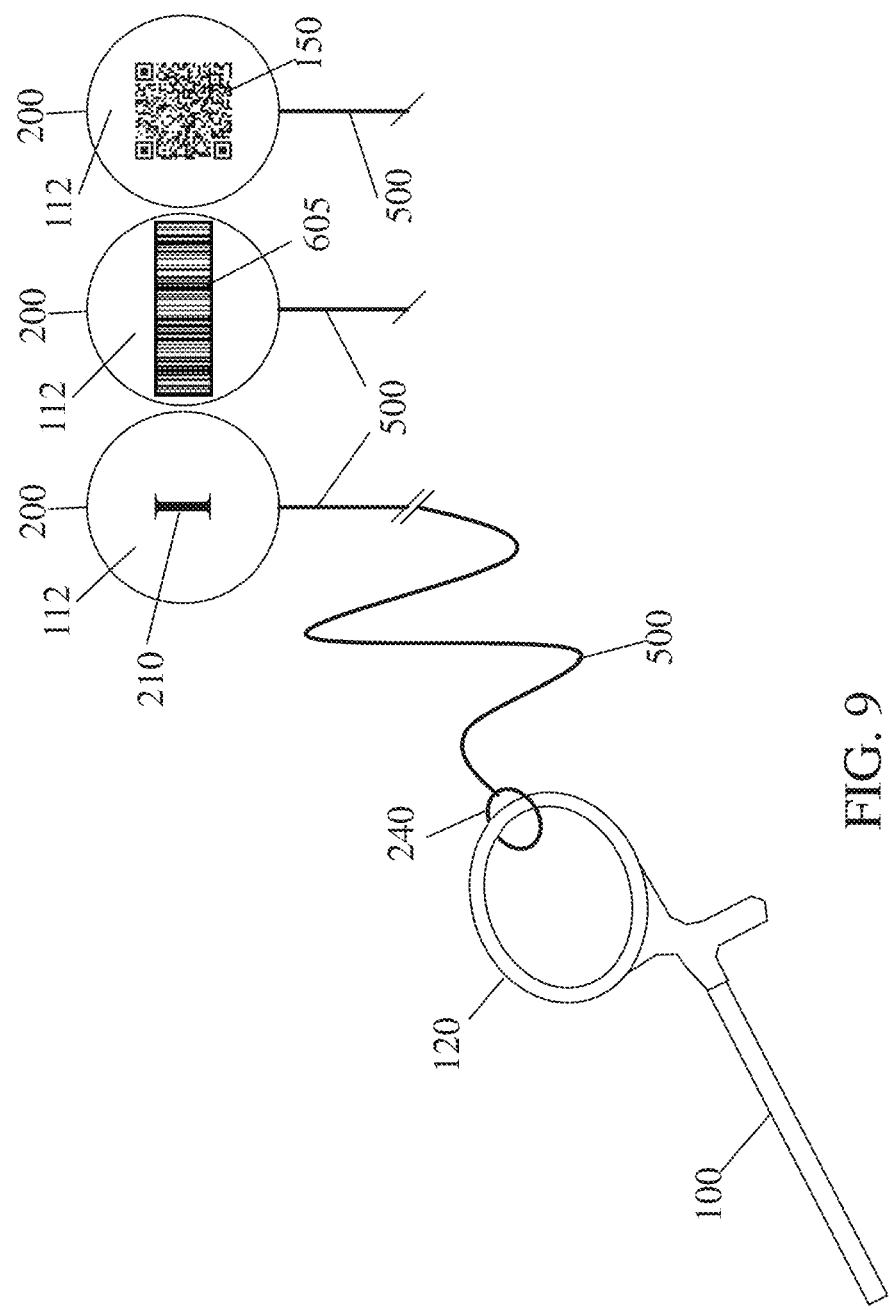
FIG. 9 shows a forceps with a stringer and tracking tag attached via a generalized retainer.

FIG. 9 shows a forceps finger ring 120 and a tracking tag 200 affixed to the instrument 100 using a stringer 500, forming a lanyard, and a generalized retainer 240. The tracking tag 200 is shown as a sphere or ball in this embodiment, but may take various other forms such as cubes, tetrahedra, flat plates, disks, or other 3-dimensional forms in a variety of sizes. Similarly, as with other embodiments, the tracking tag 200 may carry indicia identifying specific instruments or sets of instruments on the stringer. Examples include human readable characters 210, for example "I" indicating an instrument 100, computer readable characters such as bar codes 610 or Q-codes 150, or user generated peel-and-stick labels 610 carrying identifying information. In these embodiments, human readable characters 210 are also applied using contrasting vibrant coatings 112. For example, if the tracking tag 200 is a bright orange color, human readable characters 210 are preferably bright green or another vibrant contrasting color. Alternatively or additionally, computer readable optical codes 150, 605 such as bar codes or Q codes are applied to the tracking tag 200 preferably using vibrant colors that contrast with the vibrant coating 112. Further, in some embodiments, the tracking tag 200 is directly written on, for example with permanent marker, or a small length of surgical tape is applied to the tracking tag 200 and written on.

Tracking tags 200 may be constructed from a variety of materials, including, but not limited to, plastics (e.g., polyetherimide, polycarbonate, or polysulfone), stainless steel, or other materials that are biologically compatible. Plastics are preferably used in disposable designs, while stainless steel is preferred for designs that are going to be sterilized. In either case, a vibrant coating 112 as described herein is preferably applied to the tracking tag 200, stringer 500, and retainer 240.

The stringer 500 is preferably constructed in any desired length, and also from a variety of materials including, but not limited to, disposable natural or synthetic fiber threads, a polymer monofilament, thin stainless steel wire, or other flexible wire, cord, or filament. The material of the stringer 500 is preferably hypoallergenic, biocompatible, and nontoxic. Regardless of the material used, the stringer 500 preferably has a vibrant coating 112 applied to it, or incorporated in the material it is constructed from.

The retainer 240 may be constructed from a variety of materials, including, but not limited to, plastics (e.g., polyetherimide, polycarbonate, or polysulfone), stainless steel, or other materials that are biologically compatible. Plastics are preferably used as they provide an inexpensive material that is at the same time rigid enough to remain in place, yet flexible enough to allow bending to attach the retainer 240 to an instrument 100. However, metallic retainers 240 may also be used when appropriate hinge and clasp mechanisms are incorporated, and provide the additional benefit of being reusable. Alternatively, metallic retainers 240 of thin construction may also provide a similar semi-rigid material of manufacture. Regardless of construction, the retainer 240 preferably includes a vibrant coating 112 as described herein, a photo-reactive coating in the preferred range of 345-375 nm, a phosphorescent coating, or a combination thereof. The vibrant coating 112 may be formed as a separate external surface layer, or may be created by incorporating appropriate pigments described herein into the material of manufacture of the retainer 240 so they are visible on its external surface.

FIGS. 10A-10 H illustrate various embodiments of the generalized retainer 240 shown in FIG. 9. FIGS. 10A-10B show a split-ring retainer 300. The split-ring retainer 300 is preferably made of a material including, but not limited to, a resilient plastic, hardened rubber, thin stainless steel, or another semi-rigid resilient flexible material. In some preferred embodiments, ears 320 on the split-ring retainer 300 are added to assist in opening the slit 310 so that the split-ring retainer 300 may be placed on an instrument 100.

Once opened and placed over the appropriate portion of a surgical instrument 100, for example a forceps finger loop 120, the ears 320 are released, closing the slit 310. The natural resiliency of the split-ring retainer 300 material then keeps the split-ring retainer 300 closed, grasping the instrument 100.

In some embodiments, the stringer 500 is molded into the split-ring retainer 310. In other embodiments, shown in 10A, the stringer 500 is passed through an aperture 321 incorporated in the split-ring retainer 310 and is thus able to be connected to further surgical objects 100. Alternatively, as shown in FIG. 10B, the stringer 500 may be knotted around the aperture 321, or itself, to terminate a stringer 500 of surgical objects 100, or a removable tracking tag 520, 530 may be added to the stringer 500 as a terminator. The split ring retainer 300 also preferably has a vibrant coating 112.

FIGS. 10C-10D show an orifice retainer 330 having a plurality of flexible wings 340 shaped to fit an orifice in an instrument 100, in this example the space internal to a forceps finger loop 120. The orifice retainer 330 is preferably made of a material including, but not limited to, plastic, hard rubber, thin stainless steel, or another semi-rigid material that allows for a spring action in the wing 340. In some embodiments, the wings 340 are shaped to conform to specific instruments 100, so the orifice retainer 330 can be rapidly inserted or removed.

The orifice retainer 330 also has a central core having an aperture 331 through which the stringer 500 may pass. As described for the split-ring retainer 300, the stringer 500 may be molded into the orifice retainer 330, or as shown in FIG. 10D, passed through an aperture 331 for connection to further surgical objects 100, or passed through the aperture 331 and knotted to terminate the end of the stringer system 500. Alternatively, as in other embodiments, a removable tracking tag 520, 530 may be added to the stringer 500 as a terminator. The orifice retainer 330 also preferably has a vibrant coating 112.

Figure 10F:
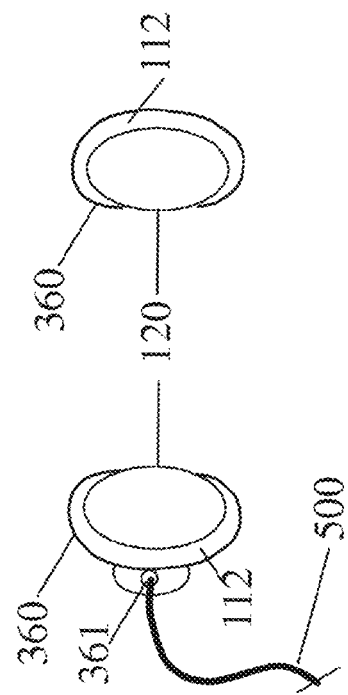
FIG. 10F shows a cross-section of a C-type retainer attached to a forceps.
Figure 10H:
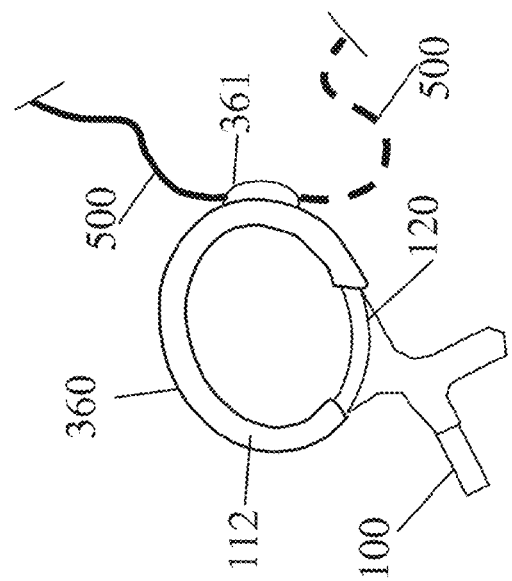
FIG. 10H shows a cross-section of a sheath retainer attached to a forceps.
Figure 10E:
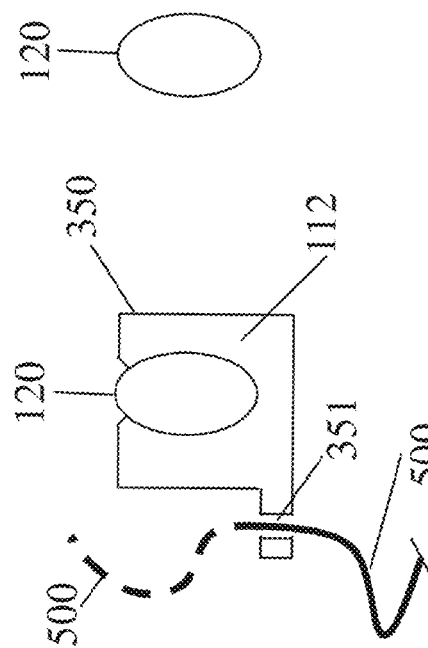
FIG. 10E shows a C-type retainer attached to a forceps.

FIGS. 10E-10F show a simple C-type retainer 350 having a space formed to substantially, but not completely, surround a portion of an instrument 100, in this case a forceps finger loop 120, providing a location for an aperture 351 through which the stringer 500 may be passed. The C-type retainer 350 is preferably made of a material including, but not limited to, plastic, hard rubber, thin stainless steel, or another semi-rigid material that allows for a spring action allowing the C-type retainer 350 to be pressed over a portion of a surgical object 100 and then remain firmly in place. As with other embodiments described herein, the stringer 500 may be molded into the C-type retainer 350. Preferably, as shown in FIG. 10F, the stringer 500 is passed through the aperture 351 for connection to further surgical objects 100, passed through the aperture 351 and knotted to terminate the end of the stringer system 500, or a removable tracking tag 520, 530 may be added to the stringer 500 as a terminator. The C-type retainer 350 also preferably has a vibrant coating 112.

Figure 10G:
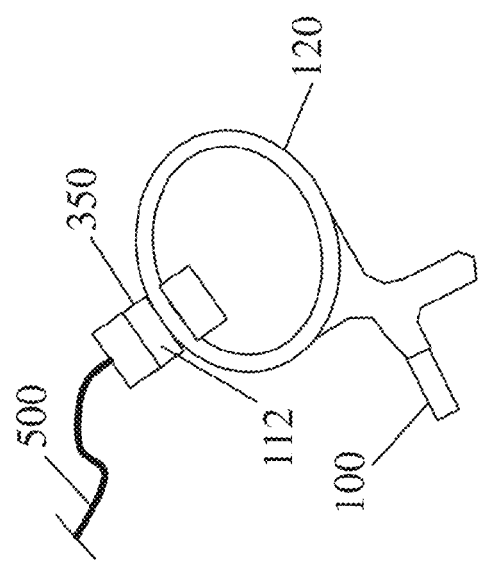
FIG. 10G shows a sheath retainer attached to a forceps.

FIGS. 10G-10H show a sheath retainer 360 which substantially, but not completely, surrounds a portion of the instrument 100, and conforms to the shape of the instrument 100 over a portion of its construction. To achieve this flexibility, the sheath retainer 360 is preferably made of a material including, but not limited to, plastic, hard rubber, or another semi-rigid material that provides a high degree of resiliency allowing the sheath retainer 360 to be pressed over a portion of a surgical object 100 and then remain firmly in place. In one preferred embodiment, the sheath retainer 360 is pressed onto the instrument 100, starting at one end, continuing along its length, until it is completely in place on the instrument 100.

In the example shown in FIGS. 10G-10H, the sheath retainer 360 conforms to a forceps finger loop 120, and provides an aperture 361 through which the stringer 500 may pass. This embodiment does not significantly interfere with manipulation of the instrument 100, even when the tracking tag 200 and stringer 500 are in place on the instrument 100. As with other embodiments described herein, the stringer 500 may be molded into the sheath retainer 360. Preferably, as shown in FIG. 10G, the stringer 500 is passed through the aperture 361 for connection to further surgical objects 100, passed through the aperture 361 and knotted to terminate the end of the stringer system 500, or a removable tracking tag 520, 530 may be added to the stringer 500 as a terminator. The sheath retainer 360 retainer 350 also preferably has a vibrant coating 112.

Regardless of the specific type of retainer 240, 320, 330, 350, 360, employed, in preferred embodiments, a tracking tag 200 may be attached to each instrument 100, or set of instruments 100, during surgical preparation, or when a new instrument 100 is added to the instrument tray during surgery. Tracking tags 200, 520, 530 and retainers 240, 320, 330, 350, 360 may be removed and left on the instrument tray when the instrument 100 is in use, and replaced when the instrument 100 is returned to the instrument tray or quarantine after use.

Alternatively, a single stringer 500 may be used with a variety of retainers 240, 320, 330, 350, 360, to connect multiple surgical objects 100 using removable tracking tags 520, 530 as described herein in embodiments where sponges 400 are connected.

Further, when a sufficiently long stringer 500 is used, tracking tags 200, 520, 530 may remain connected to surgical instruments 100 during surgery giving an unmistakable indication of where certain surgical instruments 100 are located during the procedure, and more importantly, ensuring that no surgical objects 100 remain in the patient at the time of closing.

For example, after placing a surgical object 100 in the surgical field, the stringer 500 may be oriented through a non-critical portion of the surgical field, and the tracking tag 200, 520, 530 taped or otherwise affixed to the patient or surgical drapes for organizational purposes and later recovery.

Regardless of which of the previously described methods of attachment are used, at the end of surgery, every surgical object 100 (or plurality of surgical objects 100 connected via a single stringer 500) must have its corresponding stringer 500 and tracking tag 200, 520, 530 attached, ensuring that all tracking tags 200, 520, 530 and their corresponding instruments 100 are accounted for. In some preferred embodiments, computer scanning before and after the operative procedure logs the tracking tags 200, 520, 530. In other preferred embodiments, the tracking tags 200, 520, 530 are manually logged.

While a forceps is shown in FIG. 10A-10G in conjunction with a variety of retainers 240, 320, 330, 350, 360, the stringer 500 system along with properly adapted retainers 240, 320, 330, 350, 360, may be used with virtually any surgical object 100, including, but not limited to, surgical clamps of various design, retractors, mechanical cutters, chisels, suction tips and tubes, calipers, and scalpel handles, whether reusable or disposable after a single use. Further, combinations of surgical instruments 100 and surgical sponges 400 on a single stringer 500 system may be configured. Such instruments are often manufactured from stainless steel, but may alternatively or additionally be constructed of synthetic materials such as polyetherimide (PEI), polycarbonate (PC), polysulfone (PS), and others.

Figure 13:
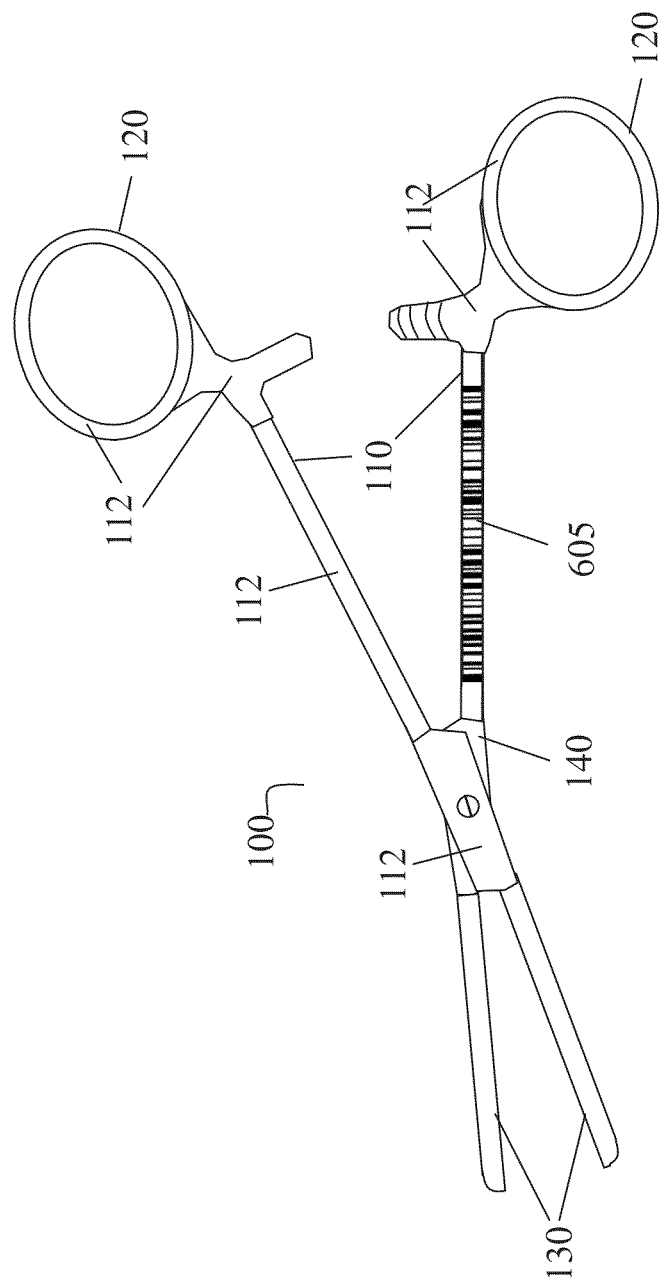
FIG. 13 shows a forceps with a vibrant coating and computer readable indicia applied.

In some embodiments, shown in FIG. 13, surgical instruments 100 are constructed specifically for use with the stringer 500 system. In FIG. 13, a generic forceps is shown. A vibrant coating 112 is preferably applied to the non-bearing surfaces of the surgical instrument 100. For example, the finger loops 120 and handles 110 of a forceps preferably include a vibrant coating 112. Regardless of type of surgical instrument 100 constructed, the vibrant coating 112 preferably includes a vibrant pigment, a photo-reactive pigment in the preferred range of 345-375 nm, a phosphorescent pigment, or a combination thereof. Further, the vibrant coating 112 may be formed as a separate exterior surface layer, or may be created by incorporating appropriate pigments into the material of manufacture of the surgical instrument 100.

Bearing surfaces, such as the jaws 130 or sliding surfaces of the scissors joint 140 preferably do not include the separate vibrant coating 112, as separate vibrant coating 112 surface layers may interfere with mating surfaces and other working surfaces that require close tolerances. In other embodiments where the vibrant coating 112 is integral to the materials of construction so that they do not interfere with the operation of the surgical instrument 100 in any way, the entire instrument 100 includes the vibrant coating 112.

The vibrant coating 112 may be applied by any method including, but not limited to, anodizing, powder coating, application of vitreous and non-vitreous ceramics, porcelain, glass, epoxy and other resin based coating methods, emulsion based coating methods, addition of pigment particles to injection molding pellets, addition of pigment particles to molten glass, or other methods, provided the final cured state of the vibrant coating 112 provides a chip-resistant biocompatible surface incorporating the high visual detectability characteristics described herein. In some preferred embodiments, the bearing surfaces 130, 140 are masked prior to application of the vibrant coating 112 during the coating process.

Figure 14A:
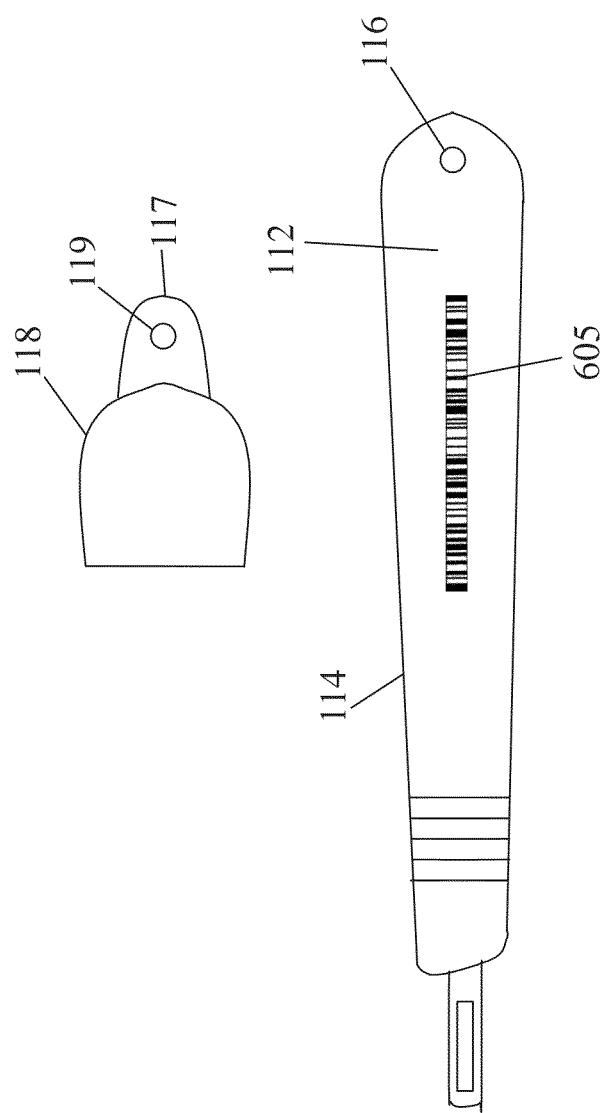
FIG. 14A shows a scalpel handle with a vibrant coating and computer readable indicia applied, as well as a retainer adapted for use with a scalpel handle.

Similarly, as shown in FIG. 14A, other types of surgical instruments such as scalpel handles may be adapted in a manner consistent with embodiments of the stringer 500 system. Application of vibrant coatings 112 is possible in both disposable, single use surgical instruments 100, and reusable surgical instruments 100. In this example, a vibrant coating 112 is preferably applied throughout the construction material, or as a discrete surface layer throughout the majority of the construction so as not to interfere with blade attachment and removal. A computer readable optical code 605 has also been preferably applied.

Surgical instruments 100 such as the scalpel handle shown in FIG. 14A may be provided with apertures 116 through which the stringer 500 may be threaded as part of their construction. Alternatively, in this example a flexible cup retainer 118 may be provided and fitted over the end of a surgical instrument 100 such as scalpel handle. The flexible cup retainer 118 is provided with a tab 117 having an aperture 119 through which the stringer 500 may be threaded.

As shown in FIGS. 14B-14D, vibrant coatings 112 and computer readable indicia (e.g., bar codes 605) may also be added to other surgical objects 100 such as surgical needles 116, sutures 118, tracking tags 113 attached to sutures 118, as well as packaging 115 used for sutures 118 and other surgical supplies that may need to be accounted for during a surgical procedure. The surgical needle 116 preferably has a vibrant coating 112 that extends approximately two-thirds of the length of the needle so as not to interfere with the sharpening of the needle point. Computer readable indicia 605 may contain a variety of data including, but not limited to, instrument type, serial number, hospital name, or other generic and specific identifiers.

A surgical suture 118 is shown in FIG. 14C as another preferred embodiment. A vibrant coating 112 has been applied as vibrant pigment particles or a vibrant emulsion added during the manufacture of the catgut, chromic catgut, polyglycolide (PGA), polydioxanone (PDS) or other materials used to form the surgical suture 118. A tag 113 is preferably attached to one end of the surgical suture 118, and preferably has human readable characters 440 and/or computer readable optical code 605 applied for tracking purposes. In the event the surgical suture 118 is pre-packaged with a surgical needle 116, holes 117 are also perforated in the tag 113 so the needle 116 can be threaded through them after use. In this manner, both the surgical needle 116 and the unused surgical suture 118 can be accounted for and tracked.

In a related preferred embodiment shown in FIG. 14D, the packaging 115 of a surgical needle 116, surgical suture 118, or combined surgical needle 116/suture 118 set preferably has a vibrant coating 112, human readable characters 440 and/or computer-readable optical code 605 applied. Additionally, holes 117 though an area of the packaging 115 that will not compromise sterility are preferably provided for storage of the surgical needle 116 after use.

Computer readable optical codes and other indicia may be applied as part of the coating and/printing process, using pigments that contrast with the underlying vibrant coating 112 to enhance their visibility. Similarly, vibrant coatings 112 may be applied during the manufacture of packaging 115.

While a forceps 100, scalpel handle 114, and needle/suture 116, 118 set have been shown in FIG. 13 and FIG. 14A-14D, the vibrant coatings 112 and other elements described herein are applicable to virtually any surgical instrument 100. These examples should not be considered limiting on the application of the vibrant coating 112, the stringer 500 system, properly adapted retainers 240, 320, 330, 350, 360, or other elements described herein, as these embodiments may be readily adapted to virtually any surgical instrument 100, including, but not limited to, surgical clamps of various design, retractors, mechanical cutters, chisels, suction tips and tubes, and calipers, whether reusable or disposable after a single use.

Figure 15:
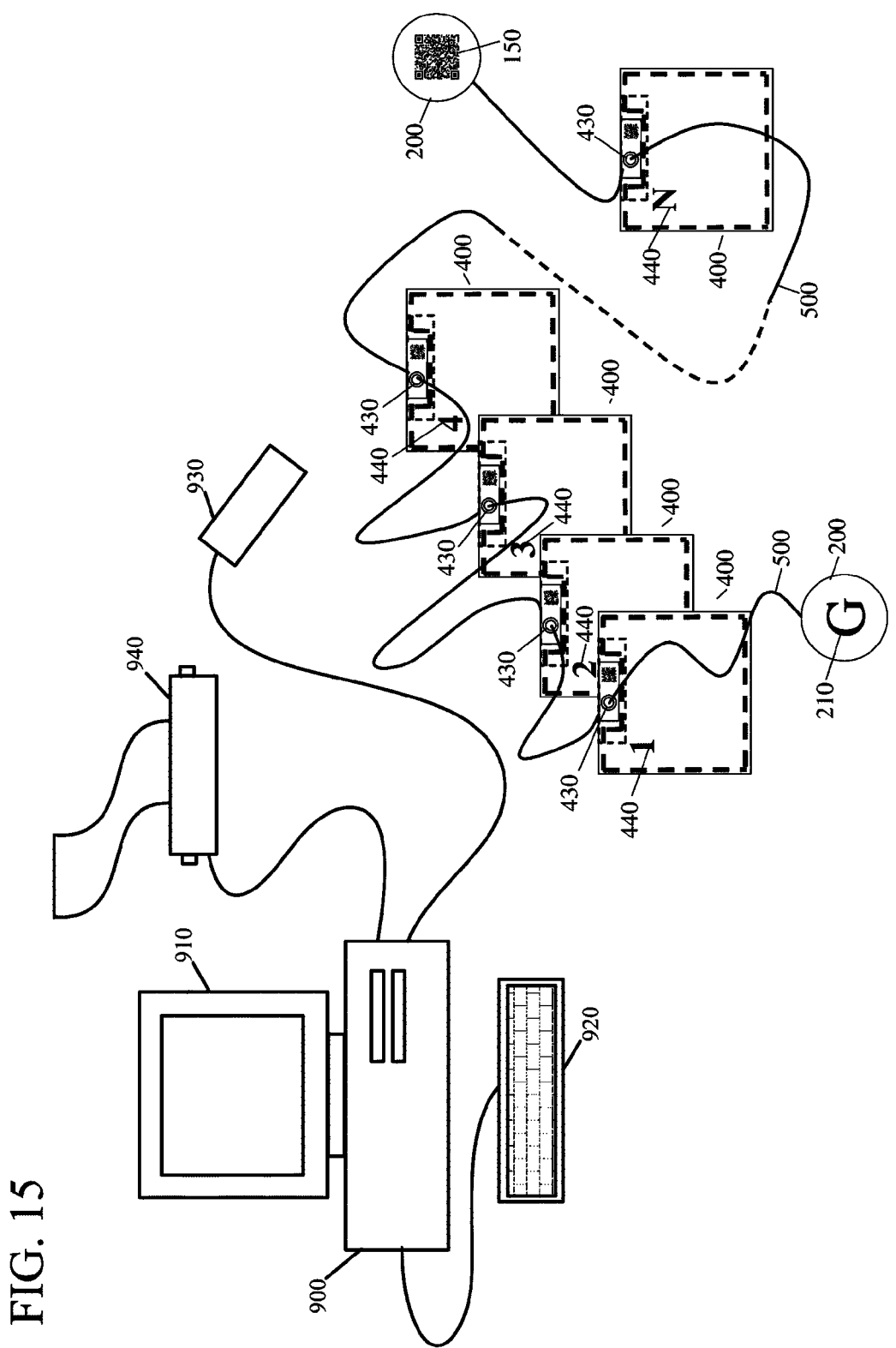
FIG. 15 shows a computer configuration used to automate data collection and verification of surgical object placement and retrieval.

In some embodiments, computer scanning before and after the operative procedure logs the tracking tags 200, 520, 530 and data identifying the surgical objects 100, 400 connected via the stringer 500. As shown in FIG. 15, a logging system including a computer 900, display 910, keyboard 920, an input device 930 capable of scanning computer readable indicia (e.g. a Q-code 150 in FIG. 15), and a printer 940 may be employed for this purpose, in conjunction with appropriate database software.

In some embodiments, prior to a surgical procedure, data identifying surgical objects (in this example, sponges 400) attached to each stringer 500 are entered into a first database record. These data may be entered manually via a keyboard, or when present, by scanning computer readable indicia 150, 605 on each surgical object 100, 400, and/or on a tracking tag 200, 520, 530 attached to a stringer. These data are saved, and one or more peel-and-stick labels 620 may be printed with human readable characters and/or computer readable indicia (a Q-code 150, for example). In other embodiments, the tracking tag 200, 520, 530 attached to a stringer 500 has been previously encoded with data identifying the surgical objects 100, 400 connected by the stringer 500, and may be scanned to enter that data into the first data base.

When the stringer 500 and the surgical objects 100, 400 connected by it are removed from the surgical field, the computer readable indicia 150, 605 on the tracking tag 200, 520, 530 may be scanned, along with computer readable indicia 150, 605 on the surgical objects 100, 400 to create a second record of surgical objects 100, 400 removed from the surgical site. The corresponding first record is then compared to this second record to verify that all surgical objects 100, 400 introduced to the surgical field have been recovered. Alternatively, computer readable indicia (e.g., a Q-code 150) on the tracking tag 200, 520, 530 can be scanned, and the surgical objects 100, 400 attached to that stringer 500 may be entered into the second record manually. Again, the corresponding first record is compared to the second record to verify that all surgical objects 100 introduced to the surgical field have been recovered.

The embodiments discussed herein are not limited to use in the surgical environment alone. The placement of objects in the body by first responders is also of concern, and the objects used in that context include many of the same types of objects used in hospital surgical settings. As such, all of the embodiments described herein are also directly applicable to ambulance operations, field medic stations, mobile military surgical facilities, and other general medical settings where significant invasive trauma and treatment can be expected. The term "surgical field", described herein, encompasses the traditional surgical environment in a hospital, as well as all of these alternative settings, as well as veterinary procedures.

For example, vibrant surface coatings 112 and other coding schema described herein may also be readily adapted to ambulance inventory procedures. Custom printing, or even specific patterned (e.g., stripes, dots, waves, etc.) vibrant color schemes may be assigned to various municipal and private emergency response units and applied to all surgical objects 100, 400 and other objects each first response provider may use in an invasive manner. Further, veterinary surgical objects are also within the scope of the embodiments discussed.

The stringer 500 embodiments described herein also provide a method that tracks and reliably recovers surgical objects from a surgical field. In preferred embodiments, the method includes the steps of placing a plurality of surgical objects 100, 400 connected by the stringer 500 system, into a surgical field. When the surgical objects 100, 400 are no longer needed in the surgical field, the stringer 500 is followed from a tracking tag 200, 520, 530 at one end of the stringer 500, along the stringers 500 course through the surgical field to the tracking tag 200, 520, 530 at the other end of the stringer 500, and the surgical objects 100, 400 in the surgical field are removed as they are encountered. Any stringer systems 500 discussed herein, including, but not limited to, elements including tracking tags 200, 520, 530 and retainers 240, 320, 330, 350, 360, may be used in this method.

In some embodiments, the number of pads 400 used is confirmed by noting the lowest numbered unused pad 400 remaining in prep inventory at the end of the surgical procedure. In the event pads 400 may have stuck together, the likelihood of overlooking a pad 400 is reduced, as the most probable event is that it has stuck to another pad 400 close in numerical sequence to the missing pad 400. For example, having noted that pads 400 number 1 through 77 are used in a procedure, but not being able to account for pad 400 number 34, the most likely place to look for the missing pad 400 would be stuck to one of pads 400 numbered 30-33 or 35-40 that were likely placed in the body at or near the same time and location.

In other preferred embodiments of the method, surgical objects 100, 400 are accounted for after removal from the surgical field. The method of accounting for surgical objects 100, 400 after removal from the surgical field may vary. Manual entry of identifying data may be performed in a log book, or in a computer database, prior to using the surgical objects 100, 400, and after their retrieval for comparison purposes. Similarly, identifying data may be scanned into a computer 910 via computer readable indicia 150, 605 on the stringer 500 elements and surgical objects 100, 400 when available. Scanning prior to use, and again after removal from the surgical field provides two data base records that may then be used for comparison purposes, and preferably includes a time-stamp of each scan.

Accounting for surgical objects 100, 400 in the method may also be enhanced by printing peel-and-stick labels 620 with identifying data such as human readable indicia 440 and computer readable indicia 150, 605. In some embodiments, labels 620 may be affixed to tracking tags 520, 530. In addition, or alternatively, peel-and-stick labels 620 may be affixed to a tote board 610 that has an "In Use" area to accept the peel-and-stick labels 620 during a surgical procedure. The peel-and-stick labels 620 may be re-affixed to an "Accounted For" area of the tote board 610 once the respective surgical objects 100, 400 have been recovered and accounted for.

The method is also applicable to a wide range of surgical objects 100, 400 such as surgical pads 400 and a variety of surgical instruments 400, including but not limited to, scalpels, forceps, retractors, and clamps. The stringer 500 may be connected to multiple surgical objects 100, 400. In other embodiments of the method, the stringer 500 is used in conjunction with a single surgical object 100, 400, and a single tracking tag 200, 520, 530, forming a lanyard with the same properties of the stringer 500.

In preferred embodiments, the method also includes the use of vibrant color pigments, phosphorescent, and/or photo-reactive pigments incorporated into the external surfaces of any or all of the stringer 500 elements in various combinations of vibrant color, fluorescence (e.g., in the range of 345-375 nm), and phosphorescence.

Figure 16:
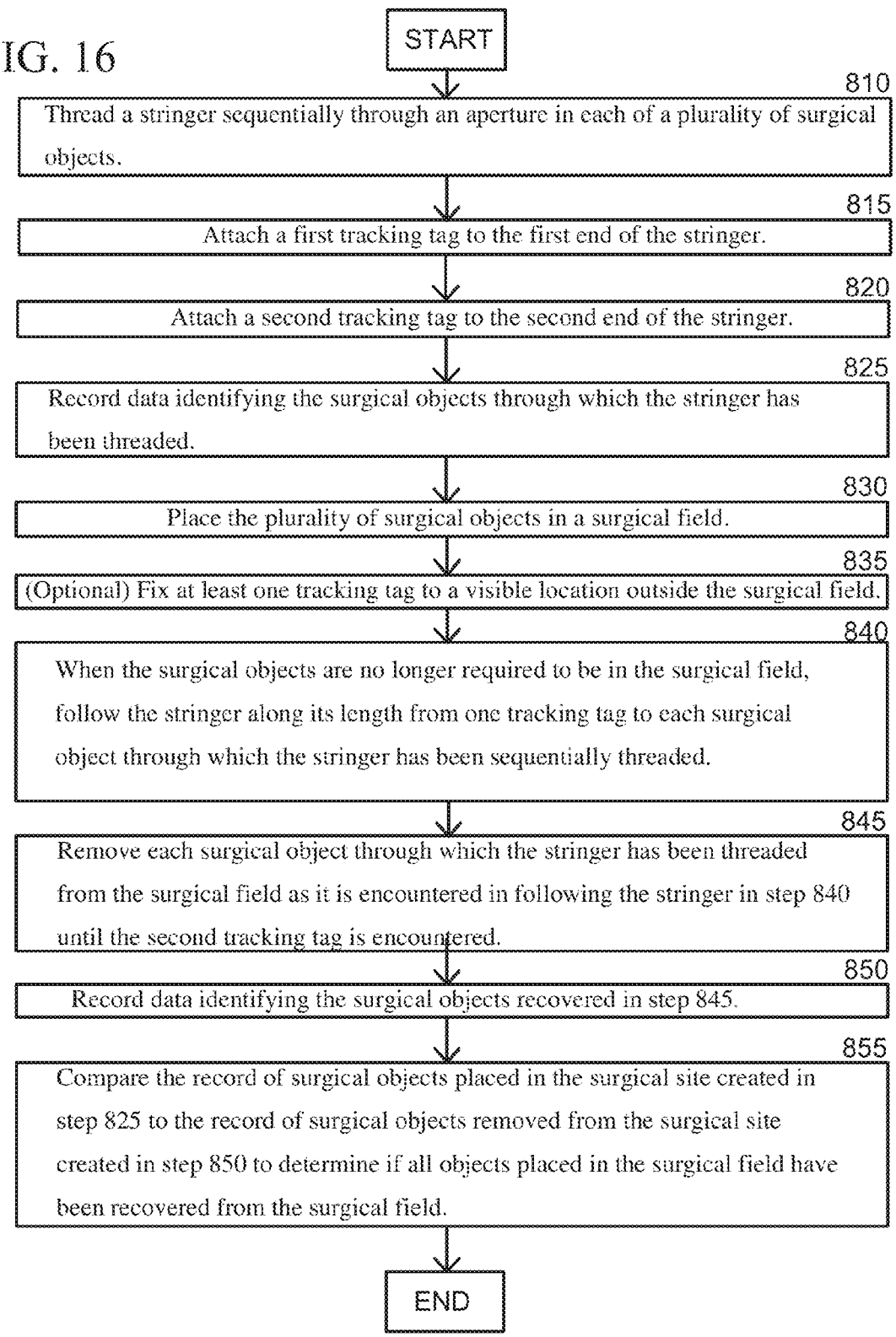
FIG. 16 shows the steps of a method for tracking surgical objects using the embodiments described herein.

A detailed listing, as shown in FIG. 16, of one embodiment of the method, can be summarized by the following steps:

Step 810: Thread a stringer sequentially through an aperture in each of a plurality of surgical objects;

Step 815: Attach a first tracking tag to the first end of the stringer;

Step 820: Attach a second tracking tag to the second end of the stringer;

Step 825: Record data identifying the surgical objects through which the stringer has been threaded;

Step 830: Place the plurality of surgical objects in a surgical field;

Step 835: (Optional) Fix at least one tracking tag to a visible location outside the surgical field;

Step 840: When the surgical objects are no longer required to be in the surgical field, follow the stringer from one tracking tag along its length to each surgical object through which the stringer has been sequentially threaded;

Step 845: Remove each surgical object through which the stringer has been threaded from the surgical field as it is encountered in following the stringer in step 840 until the second tracking tag is encountered;

Step 850: Record data identifying the surgical objects recovered in step 845; and Step 855: Compare the record of surgical objects placed in the surgical site created in step 825 to the record of surgical objects removed from the surgical site created in step 850 to determine if all objects placed in the surgical field have been recovered from the surgical field.

Figure 17:
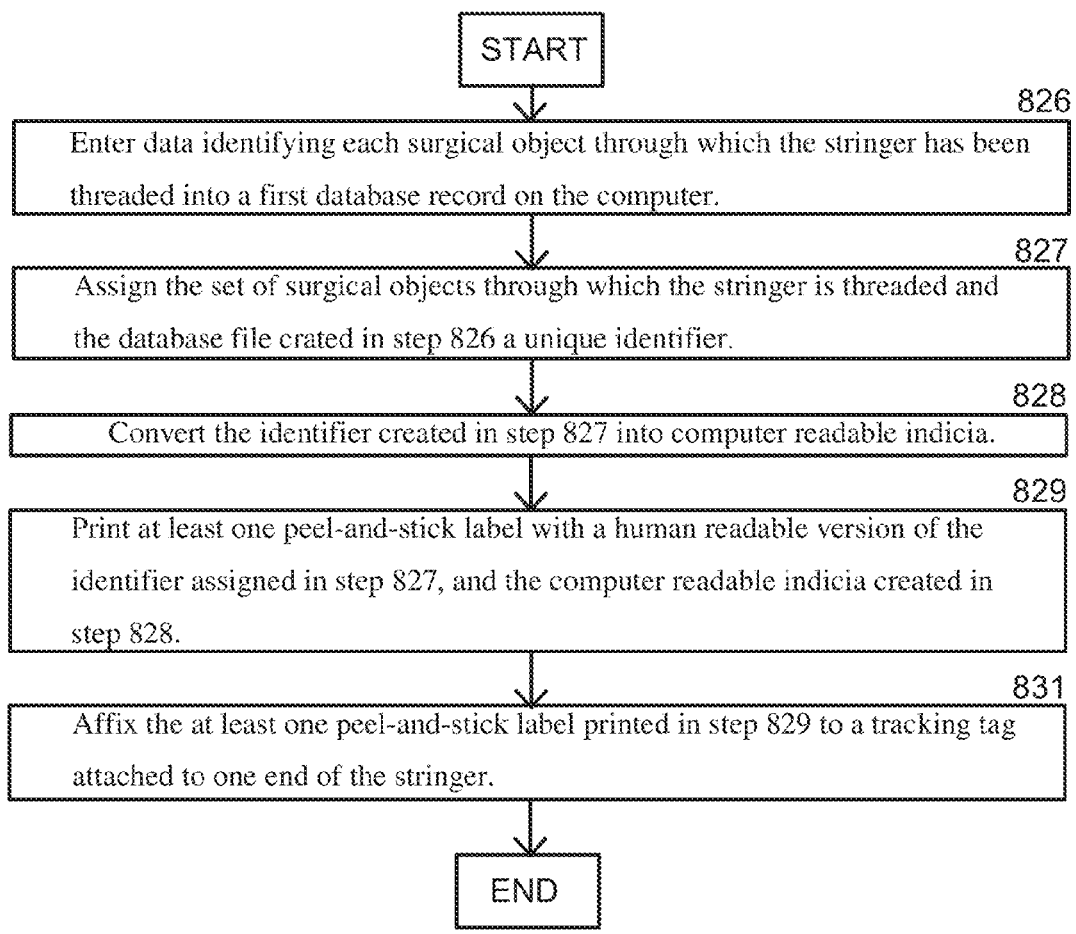
FIG. 17 shows an alternate embodiment of the method shown in FIG. 16.
Figure 18:
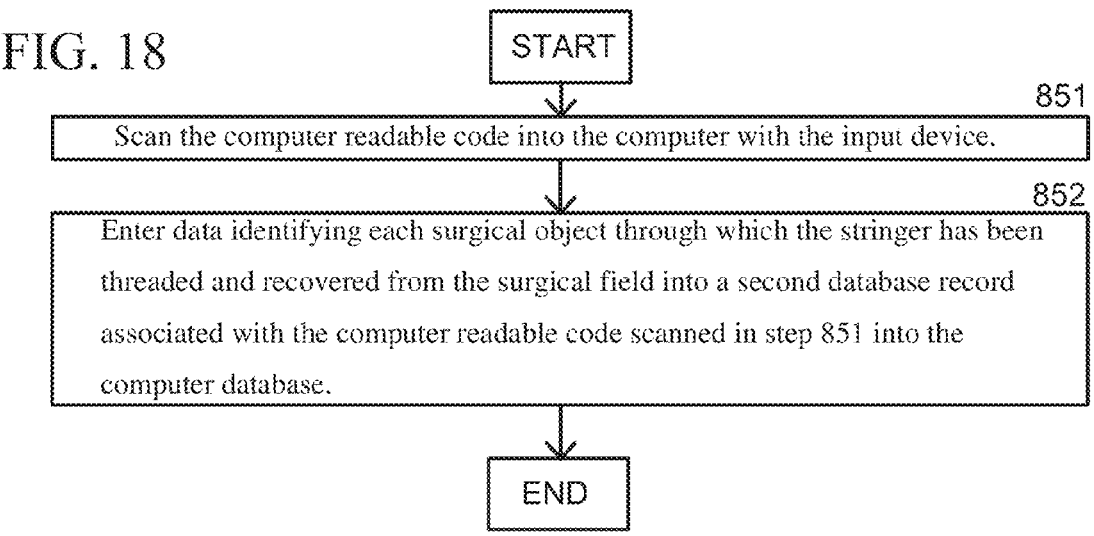
FIG. 18 shows an alternate embodiment of the method shown in FIG. 16.
Figure 19:
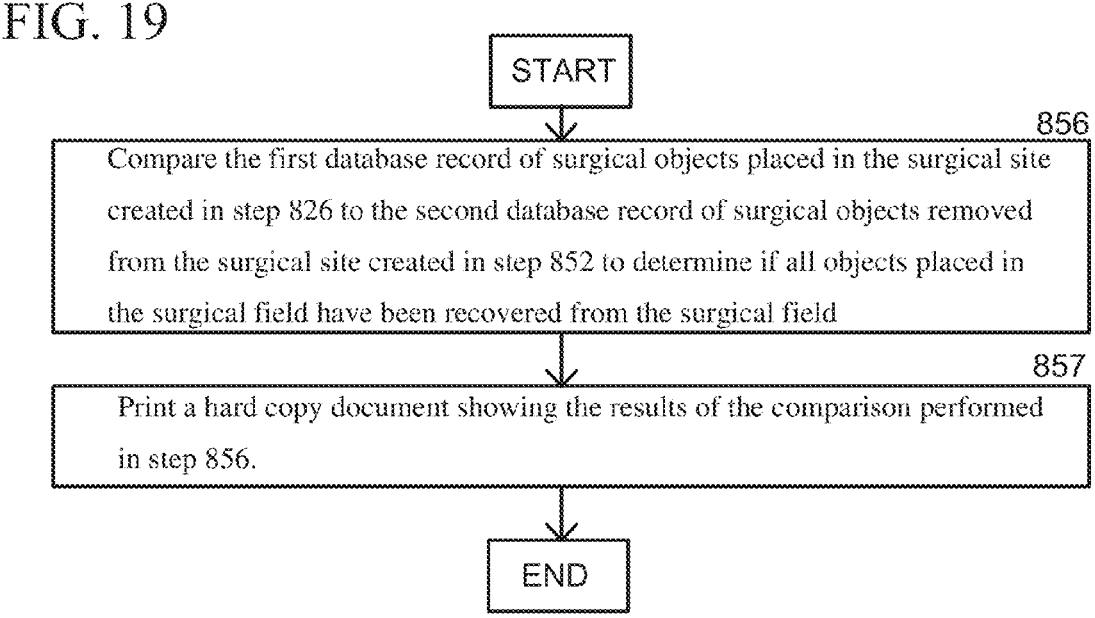
FIG. 19 shows an alternate embodiment of the method shown in FIG. 16.

As shown in FIGS. 17-19, the method shown in FIG. 16 may be modified in alternate embodiments in which the tracking system further includes a computer 900, a monitor 910, a keyboard 920, an input device 930, a database, and a printer 940. In these embodiments, Step 825 (FIG. 17) is modified to include the following steps summarized as:

Step 826: Enter data identifying each surgical object through which the stringer has been threaded into a first database record on the computer;

Step 827: Assign the set of surgical objects through which the stringer is threaded and the database file created in step 825 A above a unique identifier;

Step 828: Convert the identifier created in 825 B above into computer readable indicia;

Step 829: Print at least one peel-and-stick label with a human readable version of the identifier assigned in step 825 B above, and the computer readable indicia created in step 825 C above; and Step 831: Affix the at least one peel-and-stick label printed in step 825 D to a tracking tag attached to one end of the stringer.

In this alternate embodiment, Step 850 (FIG. 18) is modified as follows:

Step 851: Scan the computer readable code into the computer with the input device; and Step 852: Enter data identifying each surgical object through which the stringer has been threaded and recovered from the surgical field into a second database record associated with the computer readable code scanned in step 851 into the computer database.

In this alternate embodiment, Step 855 (FIG. 19) is modified as follows:

Step 856: Compare the first database record of surgical objects placed in the surgical field created in step 825 to the second database record of surgical objects removed from the surgical field created in step 850 to determine if all objects placed in the surgical field have been recovered from the surgical field; and Step 857: Print a hard copy document showing the results of the comparison performed in step 856.

Figure 20:
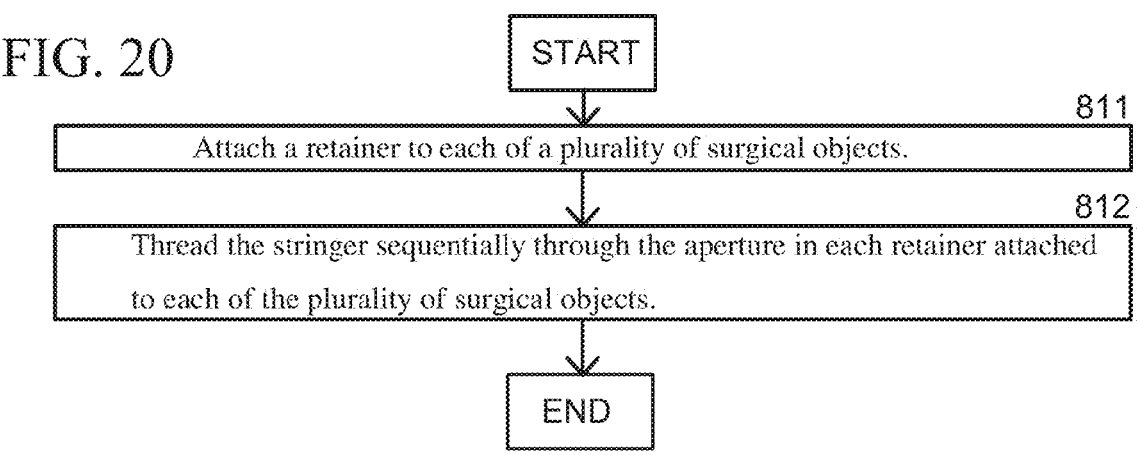
FIG. 20 shows an alternate embodiment of the method shown in FIG. 16.

In some embodiments, the tracking system further includes at least one retainer 240, 300, 330, 350, 360, and the method shown in FIG. 16, or as modified in FIGS. 17-19 and described above, may be modified according to FIG. 20. In this embodiment, Step 810 of the method (FIG. 20) above is modified to include the following steps summarized below:

Step 811: Attach a retainer to each of a plurality of surgical objects; and

Step 812: Thread the stringer sequentially through the aperture in each retainer attached to each of the plurality of surgical objects.

Accordingly, it is to be understood that the embodiments of the invention herein described are merely illustrative of the application of the principles of the invention. Reference herein to details of the illustrated embodiments is not intended to limit the scope of the claims, which themselves recite those features regarded as essential to the invention.

What is claimed is:

1. An apparatus for tracking a plurality of surgical objects placed in a surgical field, comprising:
    a) a stringer having a length, a first stringer end, a second stringer end, and a stringer external surface;
    b) a first tracking tag having a first tracking tag body and a first tracking tag external surface; and
    c) a second tracking tag having a second tracking tag body and a second tracking tag external surface;
    wherein the stringer is operatively connected to each of the plurality of surgical objects along the length of the stringer;
    wherein the first tracking tag body is attached to the first stringer end;
    wherein the second tracking tag body is attached to the second stringer end; and
    wherein, when the plurality of surgical objects are placed in the surgical field, the plurality of surgical objects are accounted for and recovered from the surgical field by following the stringer from the first tracking tag to the second tracking tag.

2. The apparatus of claim 1, wherein the stringer and at least one of the plurality of surgical objects are operatively connected with an aperture in the surgical object through which the stringer passes.

3. The apparatus of claim 1, further comprising a retainer having a retainer body and a retainer external surface;
wherein the retainer body comprises an aperture through which the stringer passes; and
wherein the retainer body removably attaches to the surgical object.

4. The apparatus of claim 3, wherein the retainer external surface comprises a vibrant coating selected from the group consisting of: a) a vibrant pigment; b) a photo-reactive pigment in the range of 345-375 nm; c) a fluorescent pigment; d) a phosphorescent pigment; and e) any combination of a), b), c), and d).

5. The apparatus of claim 1, wherein at least one of the first tracking tag and the second tracking tag is removably attached to an end of the stringer.

6. The apparatus of claim 1, wherein at least one of the first tracking tag and second tracking tag carries indicia identifying the surgical objects.

7. The apparatus of claim 1, wherein the plurality of surgical objects each comprise a body made of at least one construction material, having a surgical object external surface, wherein the apparatus further comprises a first vibrant coating applied to at least a portion of an external surface selected from the group consisting of: a) a stringer external surface; b) a first tracking tag external surface; c) a second tracking tag external surface; d) a surgical object external surface; and e) any combination of a), b), c), and d).

8. The apparatus of claim 7, further comprising an illuminator that emits light in the wavelength range of 345-375 nm and illuminates at least one of: the stringer, the first tracking tag, the second tracking tag, or the surgical object, in the surgical field.

9. The apparatus of claim 7, further comprising a spectral-selective transmission filter in the wavelength range of 345-375 nm that is designed to be worn by a person viewing the surgical field and illuminates at least one of: the stringer, the first tracking tag, the second tracking tag, or the surgical object, in the surgical field.

10. The apparatus of claim 7, further comprising a second vibrant coating applied to an external surface selected from the group consisting of:
a) a first tracking tag external surface;
b) a second tracking tag external surface;
c) a surgical object external surface; and
d) any combination of a), b), and c);
wherein the second vibrant coating forms human-readable characters.

11. The apparatus of claim 7, in which the first vibrant coating is applied to the external surface as a discrete layer.

12. The apparatus of claim 7, in which the first vibrant coating is created by integrating vibrant pigments into at least one of the first tracking tag, the second tracking tag, the surgical object, and the stringer.

13. The apparatus of claim 7, in which the first vibrant coating further comprises at least one photo-reactive pigment.

14. The apparatus of claim 13, in which the at least one photo-reactive pigment is selected from the group consisting of: a) a phosphorescent pigment; b) a fluorescent pigment; and c) a combination of a) and b).

15. The apparatus of claim 13, wherein the photo-reactive pigment is reactive in the wavelength range of 345-375 nm.

16. The apparatus of claim 7, wherein a first plurality of the surgical objects have a first color of the first vibrant coating and a second plurality of the surgical objects have a second color of the first vibrant coating that is different than the first color.

17. The apparatus of claim 16, wherein a color of the surgical objects alternates between the first color and the second color along the length of the stringer.

18. The apparatus of claim 1, wherein the plurality of surgical objects are surgical pads positioned along the length of the stringer.

19. The apparatus of claim 18, wherein the surgical pads comprise at least one reinforcing layer having greater mechanical strength than at least one construction material of a body of the surgical pad.

20. The apparatus of claim 19, in which a reinforcing layer of the surgical pads has an area which is approximately equal to an area of the surgical pad.

21. The apparatus of claim 20, in which at least one reinforced hole is provided through the reinforcing layer; wherein the stringer passes through the reinforced hole.

22. The apparatus of claim 20, wherein the at least one reinforcement layer carries indicia.

23. The apparatus of claim 18, wherein at least a portion of an external surface of the surgical pads have at least a first vibrant coating.

24. The apparatus of claim 18, wherein each of the plurality of surgical pads carries indicia.

25. The apparatus of claim 18, further comprising a package that comprises the surgical pads and further comprises at least one label carrying indicia identifying the plurality of surgical pads.

26. The apparatus of claim 25, further comprising a tote board having a surface to which the at least one label can be attached.

27. The apparatus of claim 26, wherein the labels are peel-and-stick labels.

28. The apparatus of claim 1, wherein the surgical object is a surgical instrument selected from the group consisting of a surgical needle, a scalpel, a forceps, a clamp, a retractor, and a length of suture material.

29. The apparatus of claim 28, wherein at least a portion of the external surface of the surgical instruments have at least a first vibrant coating.

30. An apparatus comprising:
a) a plurality of surgical pads, each comprising a body made of at least one construction material and having an external surface, at least a portion of the external surface having at least a first vibrant coating, each surgical pad further comprising at least one reinforcing layer having greater mechanical strength than the at least one construction material of the body of the surgical pad in which at least one reinforced hole is provided through the reinforcing layer; and
b) a stringer threaded through at least one reinforced hole in each surgical pad.

31. The apparatus of claim 30, wherein the stringer has a second vibrant coating.

32. The apparatus of claim 30, further comprising at least one tracking tag removably attached to the stringer.

33. The surgical object of claim 32, in which the at least one tracking tag further comprises human-readable characters applied in a vibrant coating.

34. The surgical object of claim 32, in which the at least one tracking tag further comprises a computer-readable optical code.

35. The surgical object of claim 30, in which the surgical object further comprises a first tracking tag having a first surface with a second vibrant coating attached to a first end of the stringer, and a second tracking tag with a second surface having a third vibrant coating attached to a second end of the stringer.

36. A method of tracking and recovering a plurality of surgical objects from a surgical field using a tracking system comprising a stringer having a length, a first stringer end, a second stringer end, and a stringer external surface, a first tracking tag having a first tracking tag body and a first tracking tag external surface, and a second tracking tag having a second tracking tag body and a second tracking tag external surface, wherein the stringer is operatively connected to each of the plurality of surgical objects along the length of the stringer, wherein the first tracking tag body is attached to the first stringer end, and wherein the second tracking tag body is attached to the second stringer end, the method comprising the steps of:
 a) placing the plurality of surgical objects in the surgical field; and
 b) removing the plurality of surgical objects from the surgical field by following the stringer from the first tracking tag to the second tracking tag.

37. The method of claim 36, further comprising the step of:
 c) accounting for each of the surgical objects removed from the surgical field.

38. The method of claim 37, further comprising, before step a), the step of:
 d) recording data identifying the stringer and the plurality of surgical objects to which the stringer is attached;
 wherein step c) comprises the substeps of:
 i) recording data identifying the surgical objects recovered in step b); and
 ii) comparing the data recorded in substep i) with the data recorded in step d).

39. The method of claim 37, further comprising, before step a), the steps of:
 d) scanning identification data encoded in computer readable code on each surgical object into a computer during a surgical procedure; and
 e) saving the identification data;
 wherein step c) comprises the substeps of:
 i) scanning identification data encoded in computer readable code on each of the surgical objects at surgical procedure termination; and
 ii) comparing the identification data saved in step (e) to the identification data scanned in substep (i) to identify surgical objects which were not scanned.

40. The method of claim 37, further comprising, before step a), the steps of:
 d) printing stickers with surgical object identification information, each sticker bearing identification information of a corresponding surgical object; and
 e) posting the stickers printed in step (d) on a board first area as the corresponding surgical object is placed into the surgical field;
 wherein step c) comprises the substeps of:
 i) moving the sticker corresponding to a surgical object to a board second area when the object is removed from the surgical field; and
 ii) ensuring no stickers remain in the board first area at an end of a surgical procedure.

41. The method of claim 36, wherein the stringer and at least one of the plurality of surgical objects are operatively connected with an aperture in the surgical object through which the stringer passes.

42. The method of claim 36, wherein the tracking system further comprises a retainer having a retainer body and a retainer external surface;
 wherein the retainer body comprises an aperture through which the stringer passes; and
 wherein the retainer body removably attaches to the surgical object.

43. The method of claim 36, wherein the plurality of surgical objects each comprise a body made of at least one construction material, having a surgical object external surface; and
 wherein the tracking system further comprises a first vibrant coating applied to at least a portion an external surface selected from the group consisting of: a) a stringer external surface; b) a first tracking tag external surface; c) a second tracking tag external surface; d) a surgical object external surface; and e) any combination of a), b), c) and d).

44. A method of locating surgical needles in a surgical field using a tracking tag having a vibrant coating and a surgical needle retainer on the tag, comprising:
 a) before surgery, inserting a surgical needle into the surgical needle retainer;
 b) attaching the tracking tag to a position outside a surgical field, such that the tag remains visible;
 c) removing the surgical needle from the surgical needle retainer for use; and
 d) before ending surgery, confirming that the surgical needle has been replaced in the surgical needle retainer.

* * * * *

UNITED STATES PATENT AND TRADEMARK OFFICE
CERTIFICATE OF CORRECTION

| | | |
|---|---|---|
| PATENT NO. | : 9,089,366 B2 | Page 1 of 1 |
| APPLICATION NO. | : 14/132733 | |
| DATED | : July 28, 2015 | |
| INVENTOR(S) | : Garner-Richards et al. | |

It is certified that error appears in the above-identified patent and that said Letters Patent is hereby corrected as shown below:

In the claims
   Claim 43 (Column 26, lines 31-32): replace "applied to at least a portion an external surface" with "applied to at least a portion of an external surface"

Signed and Sealed this
First Day of December, 2015

Michelle K. Lee
*Director of the United States Patent and Trademark Office*